(12) United States Patent
Smith et al.

(10) Patent No.: US 11,291,448 B2
(45) Date of Patent: Apr. 5, 2022

(54) MECHANICAL TISSUE COUPLING SYSTEM, APPLICATOR THEREFOR AND METHOD OF USE THEREOF

(71) Applicant: BandGrip, Inc., Chicago, IL (US)

(72) Inventors: Fred Smith, Houston, TX (US); Tom Pruter, Lincolnshire, IL (US); Keith Hoglund, Burr Ridge, IL (US)

(73) Assignee: BandGrip, Inc., Chicago, IL (US)

( * ) Notice: Subject to any disclaimer, the term of this patent is extended or adjusted under 35 U.S.C. 154(b) by 389 days.

(21) Appl. No.: 16/191,055

(22) Filed: Nov. 14, 2018

(65) Prior Publication Data

US 2019/0142425 A1 May 16, 2019

Related U.S. Application Data

(60) Provisional application No. 62/586,253, filed on Nov. 15, 2017.

(51) Int. Cl.
| | |
|---|---|
| *A61B 17/08* | (2006.01) |
| *A61B 17/28* | (2006.01) |
| *A61B 17/10* | (2006.01) |
| *A61B 17/064* | (2006.01) |
| *A61B 17/00* | (2006.01) |
| *A61B 17/068* | (2006.01) |

(52) U.S. Cl.
CPC ............ *A61B 17/08* (2013.01); *A61B 17/064* (2013.01); *A61B 17/10* (2013.01); *A61B 17/282* (2013.01); *A61B 17/2833* (2013.01); *A61B 17/068* (2013.01); *A61B 17/0643* (2013.01); *A61B 2017/00477* (2013.01); *A61B 2017/0641* (2013.01); *A61B 2017/081* (2013.01); *A61B 2017/2829* (2013.01)

(58) Field of Classification Search
CPC .......... A61B 17/0643; A61B 2017/081; A61B 2017/0641; A61B 2017/2829; A61B 2017/00477; A61B 17/08; A61B 17/10; A61B 17/064; A61B 17/282; A61B 17/2833; A61B 17/068; A61B 17/1285; A61B 17/128; A61B 17/083; A61B 17/12; A61B 17/1227; A61B 2017/086; A61B 2017/1125; A61B 2017/12004
See application file for complete search history.

(56) References Cited

U.S. PATENT DOCUMENTS

| | | | |
|---|---|---|---|
| 4,430,998 A | | 2/1984 | Harvey et al. |
| 4,637,380 A | * | 1/1987 | Orejola .................. A61B 17/08 606/216 |
| 5,603,145 A | | 2/1997 | Arakawa et al. |
| (Continued) | | | |

FOREIGN PATENT DOCUMENTS

SU 1165376 A1 * 7/1985

*Primary Examiner* — Melanie R Tyson
*Assistant Examiner* — Andrew P. Restaino
(74) *Attorney, Agent, or Firm* — The Watson IP Group, PLC; Jovan N. Jovanovic

(57) ABSTRACT

A mechanical tissue coupling system that includes a first side tissue grasping assembly, a second side tissue grasping assembly and a joining assembly. The joining assembly is structurally configured to join the first side tissue grasping assembly to the second side tissue grasping assembly. An applicator is likewise disclosed as is a method of using the system and the applicator.

15 Claims, 25 Drawing Sheets

(56) References Cited

U.S. PATENT DOCUMENTS

| | | | |
|---|---|---|---|
| 5,814,067 A * | 9/1998 | Fleischmann | A61B 17/08 |
| | | | 606/205 |
| 5,968,097 A | 10/1999 | Frechet | |
| 6,652,559 B1 | 11/2003 | Tetreault | |
| 6,712,830 B2 | 3/2004 | Esplin | |
| 7,156,862 B2 | 1/2007 | Jacobs et al. | |
| 8,945,156 B2 | 2/2015 | Kubiak et al. | |
| 2010/0036380 A1 * | 2/2010 | Taylor | A61B 17/00234 |
| | | | 606/52 |
| 2011/0040307 A1 * | 2/2011 | Ranchod | A61B 17/10 |
| | | | 606/142 |
| 2015/0305739 A1 | 10/2015 | Rolandi et al. | |
| 2016/0151062 A1 * | 6/2016 | Bachrach | A61B 17/064 |
| | | | 606/221 |
| 2016/0249924 A1 * | 9/2016 | Belson | A61B 17/0466 |
| | | | 606/216 |
| 2017/0333039 A1 | 3/2017 | Leung | |
| 2018/0271534 A1 * | 9/2018 | Shellenberger | A61B 17/122 |

\* cited by examiner

MECHANICAL TISSUE COUPLING SYSTEM, APPLICATOR THEREFOR AND METHOD OF USE THEREOF

CROSS-REFERENCE TO RELATED APPLICATION

This application claims priority from U.S. Pat. App. Ser. No. 62/586,253 filed Nov. 15, 2017, entitled Mechanical Coupling System and Method of Use, the entire specification of which is hereby incorporated by reference in its entirety.

This application is related, but currently does not claim priority from, copending U.S. patent application Ser. No. 15/801,529, filed Nov. 2, 2017, entitled "Bandage and Anchor For Bandages", the entirety of which is hereby incorporated by reference in its entirety. This application is also related, but currently does not claim priority from U.S. Pat. App. Pub. No. 2017/0128273, filed Nov. 11, 2016, entitled "Bandage", the entirety of which is hereby incorporated by reference in its entirety.

BACKGROUND OF THE DISCLOSURE

1. Field of the Disclosure

The disclosure relates in general to medical devices, and more particularly, to a mechanical tissue coupling system and method of using the same to couple different sides or portions of tissue together.

2. Background Art

The use of sutures or other structures to couple tissue together is known. Within the body, in particular, it is often the case that extensive tissue coupling can may require a substantial number of sutures. While sutures are certainly well known and have been utilized for long period of time, there remain problems and drawbacks.

This can be time consuming. Additionally, as sutures or the like extend through tissue, further damage to the tissue occurs. There is a need for procedures which can be accomplished faster and/or which can be accomplished with less harmful impact on the user. Such uses may extend to wounds on the surface of a patient or subcutaneously.

SUMMARY OF THE DISCLOSURE

In an aspect of the disclosure, the disclosure is directed to a mechanical tissue coupling system comprising a first side tissue grasping assembly, a second side tissue grasping assembly and a joining assembly. The joining assembly is structurally configured to join the first side tissue grasping assembly to the second side tissue grasping assembly.

In some configurations, the first side tissue grasping assembly further comprises an elongated body, a jaw coupling and a plurality of gripping structures. The elongated body has an inner end and an outer end. The jaw coupling is disposed on the elongated body. The plurality of gripping structures extending outwardly from the elongated body.

In some configurations, the jaw coupling comprises an elongated slot extending between the inner end and the outer end of the elongated body.

In some such configurations, each of the plurality of gripping structures include an upstand structure that terminates in a tip.

In some such configurations, at least a portion of the gripping structure comprises an overhang portion that extends beyond the footprint of the elongated body.

In some configurations, the tip is part of the overhang portion.

In some configurations, the plurality of gripping structures are equally spaced relative to each other while being offset and not centered relative to the elongated body.

In some configurations the first side tissue grasping assembly and the second side tissue grasping assembly are substantially identical. It is contemplated that the first side tissue grasping assembly and the second side tissue grasping assembly are one of dissolvable and non-disolvable within a body of a patient.

In some configurations, the joining assembly further comprises at least one first mating structure disposed on the first side tissue grasping assembly and at least one second mating structure disposed on the second side tissue grasping assembly.

In some configurations, the first mating structure comprises a bore extending into the elongated body, with the second mating structure comprising a tab extendable into the bore and engageable with the bore a locked engagement.

In some configurations, the first mating structure and the second mating structure define at least two locking positions, varying the space between the first side tissue grasping assembly and the second side tissue grasping assembly.

In some configurations, the first mating structure includes a retaining ledge and the second mating structure comprises an outer flange and an inner flange spaced apart from the outer flange. The outer flange is engageable with the retaining ledge to define a first locked position and the inner flange engageable with the retaining ledge to define a second locked position.

In some configurations, the first side tissue grasping assembly includes at least one first mating structure and at least one second mating structure. The second side tissue grasping assembly includes at least one first mating structure and at least one second mating structure. The at least one first mating structure of the first side tissue grasping assembly engageable with the at least one second mating structure of the second side tissue grasping assembly. The at least one second mating structure of the first side tissue grasping assembly engageable with the at least one first mating structure of the second side grasping assembly.

In another aspect of the disclosure, the disclosure is directed to an applicator structurally configured to apply a mechanical tissue coupling system. The applicator comprises forceps, a first grasping element and a second grasping element. The forceps defining a first opposing jaw and a second opposing jaw. The first opposing jaw is attached to a first opposing shank and the second opposing jaw attached to a second opposing shank and pivotably coupled by a lock. The first grasping element retainer is disposed on the first opposing jaw. The first grasping element retainer is structurally configured to allow slidable engagement of a tissue grasping assembly therealong. The second grasping element retainer is disposed on the second opposing jaw. The second grasping element retainer structurally configured to allow slidable engagement of a tissue grasping assembly thereal ong.

In some configurations, the applicator further comprises a disengaging assembly. The disengaging assembly has an actuator pivotably coupled to the first opposing shank, with a plunger slidably movable along the first opposing jaw, and a connecting rod extending between the actuator and the plunger. Pivoting of the actuator slidably moves the plunger along the first opposing jaw toward or away from a distal end of the first opposing jaw.

In some configurations, the first grasping element retainer further includes a mating structure extending along the first opposing jaw and the second grasping element retainer further includes a mating structure extending along the second opposing jaw.

In some configurations, the first grasping element retainer further includes an outer support extending along the first opposing jaw and positioned outboard of the mating structure extending along the first opposing jaw. The second grasping element retainer further includes an outer support extending along the second opposing jaw and positioned outboard of the mating structure extending along the second opposing jaw.

In some configurations, the plunger slidably moves along the mating structure extending along the first opposing jaw.

In another aspect of the disclosure, the disclosure is directed to a combination mechanical tissue coupling system and applicator. The mechanical tissue coupling system comprises a first side tissue grasping assembly; a second side tissue grasping assembly; and a joining assembly structurally configured to join the first side tissue grasping assembly to the second side tissue grasping assembly. The applicator comprises forceps, a first grasping element and a second grasping element. The forceps define a first opposing jaw and a second opposing jaw. The first opposing jaw is attached to a first opposing shank and the second opposing jaw is attached to a second opposing shank and pivotably coupled by a lock. The first grasping element retainer is disposed on the first opposing jaw. the first grasping element retainer is structurally configured to allow slidable engagement of the first side tissue grasping assembly therealong. The second grasping element retainer is disposed on the second opposing jaw. The second grasping element retainer structurally configured to allow slidable engagement of the second side tissue grasping assembly therealong.

In yet another aspect of the disclosure, the disclosure is directed to a method of coupling tissue with a mechanical tissue coupling system comprising the steps of: slidably attaching a first side tissue grasping assembly to a first grasping element retainer on a first opposing jaw of forceps; slidably attaching a second side tissue grasping assembly to a second grasping element retainer on a second opposing jaw of forceps; separating the first opposing jaw from the second opposing jaw; placing tissue to be coupled between the first side tissue grasping assembly and the second side tissue grasping assembly; engaging the tissue with gripping structures of each of the first side tissue grasping assembly and the second side tissue grasping assembly; directing the first opposing jaw toward the second opposing jaw; joining the first side tissue grasping assembly to the second side tissue grasping assembly in locked engagement; and releasing the first side tissue grasping assembly and the second side tissue grasping assembly from the first opposing jaw and the second opposing jaw.

BRIEF DESCRIPTION OF THE DRAWINGS

The disclosure will now be described with reference to the drawings wherein.

DETAILED DESCRIPTION OF THE DISCLOSURE

Figure 1:
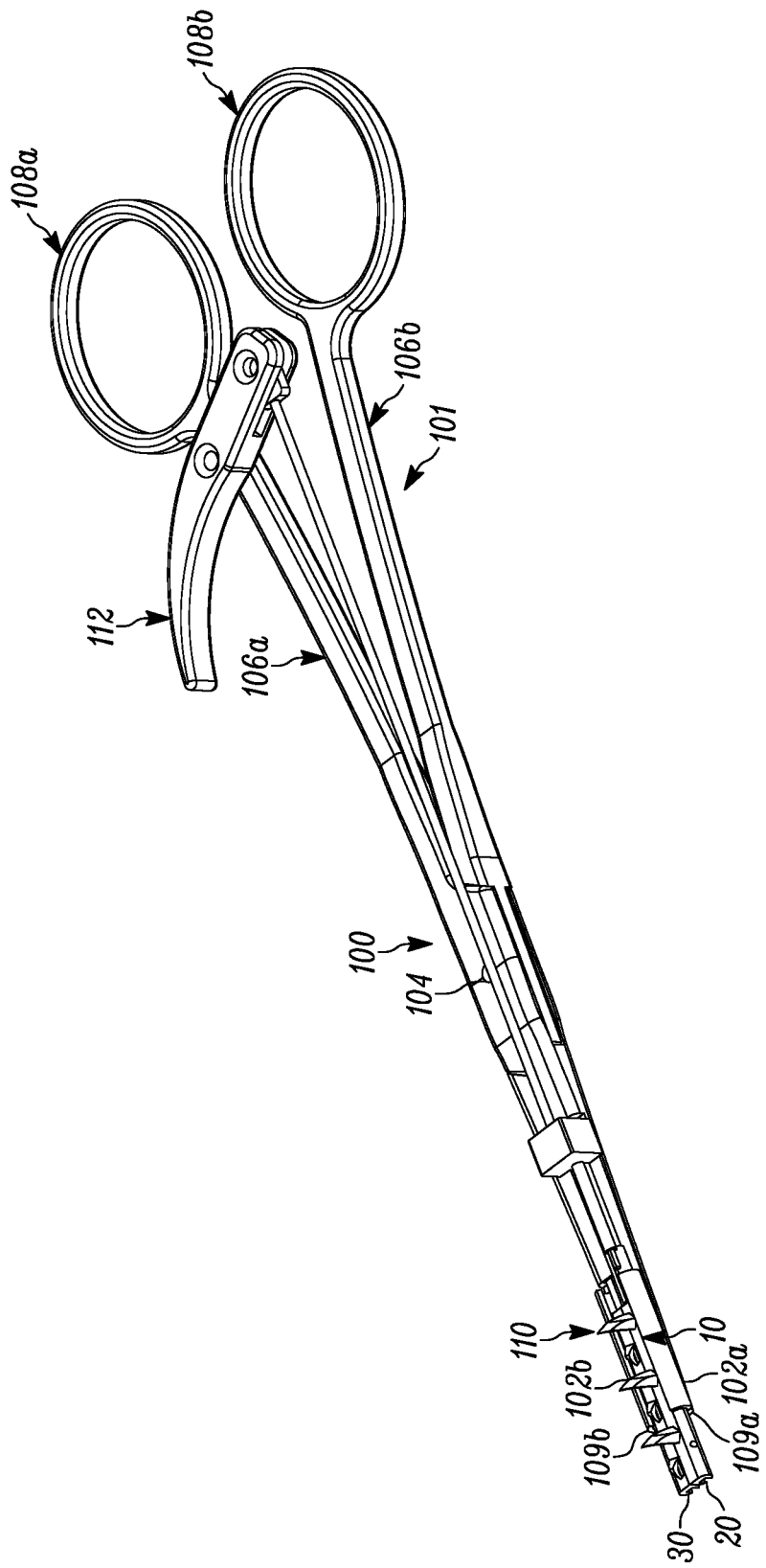
FIG. 1 of the drawings is a perspective view of the mechanical tissue coupling system and applicator of the present disclosure, showing, in particular, the system installed onto an applicator and in a locked configuration (the second position of locking therebetween)
Figure 2:
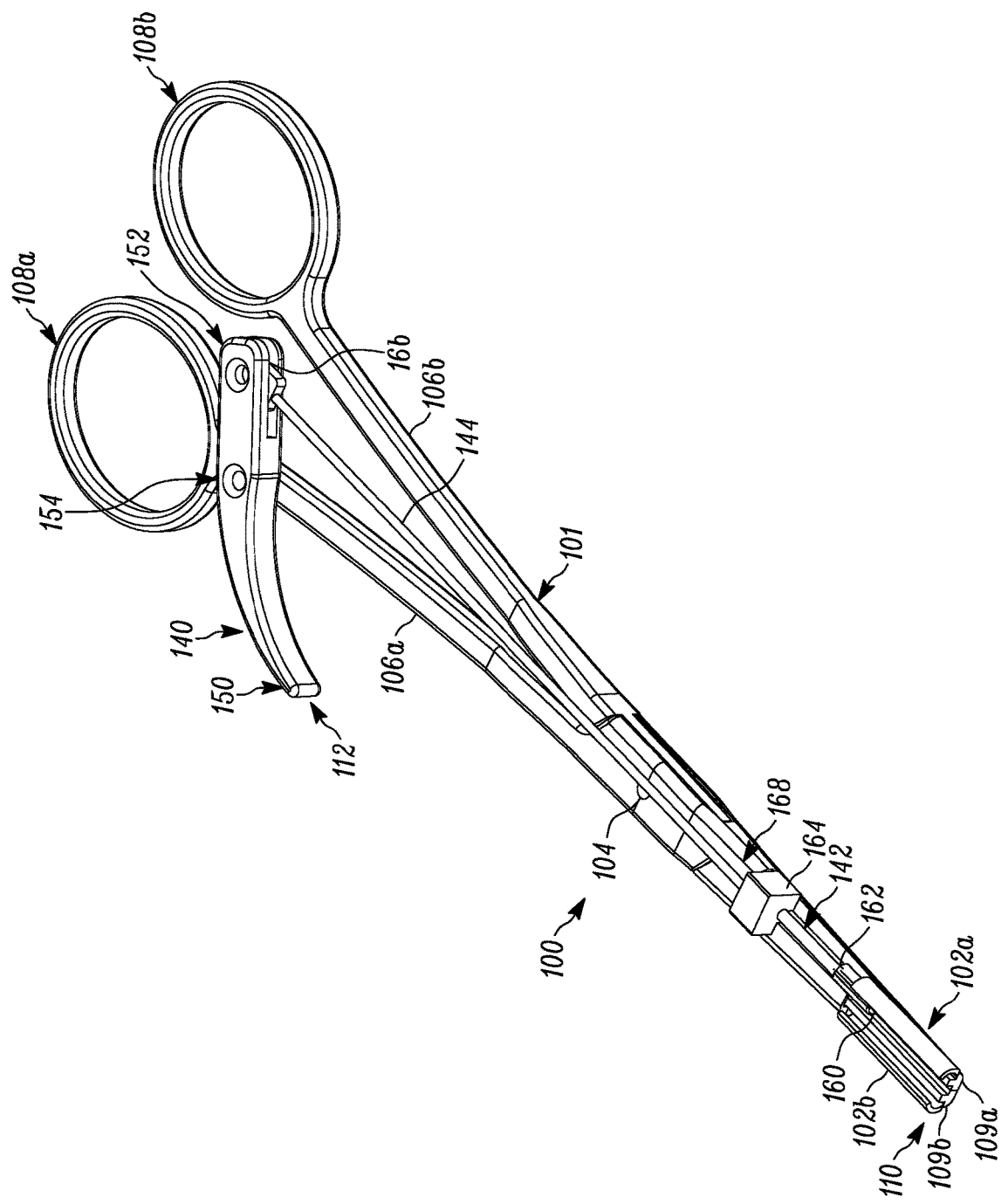
FIG. 2 of the drawings is a perspective view of the applicator of the present disclosure.

While this disclosure is susceptible of embodiment in many different forms, there is shown in the drawings and described herein in detail a specific embodiment(s) with the understanding that the present disclosure is to be considered as an exemplification and is not intended to be limited to the embodiment(s) illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Referring now to the drawings and in particular to FIG. 1, the mechanical tissue coupling system is shown generally at 10 and along with applicator 100. It will be understood that the coupling system 10 cooperates with the applicator 100 and, as such, it is contemplated that the shape of the forceps and the system substantially correspond so that the applicator can assist with the positioning and applying of the coupling system in a subcutaneous as well as in surface applications. A second configuration is shown in FIGS. 20 through 25.

In the configuration shown in FIGS. 1 through 17, and with particular reference to FIGS. 1 through 6, the applicator 100 comprises a configuration which structurally includes forceps 101 with structures that aid in the attachment of and the deploying of the mechanical tissue coupling system. The forceps 101 includes opposing jaws 102a, 102b, lock 104, opposing shanks 106a, 106b and finger rings 108a, 108b. The finger rings 108a, 108b are generally positioned at a distal end of the opposing shanks 106a, 106b, respectively. The opposing jaws 102a, 102b extend away from the lock 104 and terminate at a distal end 109a, 109b. It will be understood that the finger rings can be manipulated, which, in turn, alters the position of the opposing jaws relative to each other about lock 104. Preferably, the forceps comprise a stainless steel member that can be cleaned, sanitized and/or sterilized in an autoclave or the like. Of course, the disclosure is not limited to a particular material for the forceps.

Figure 3:
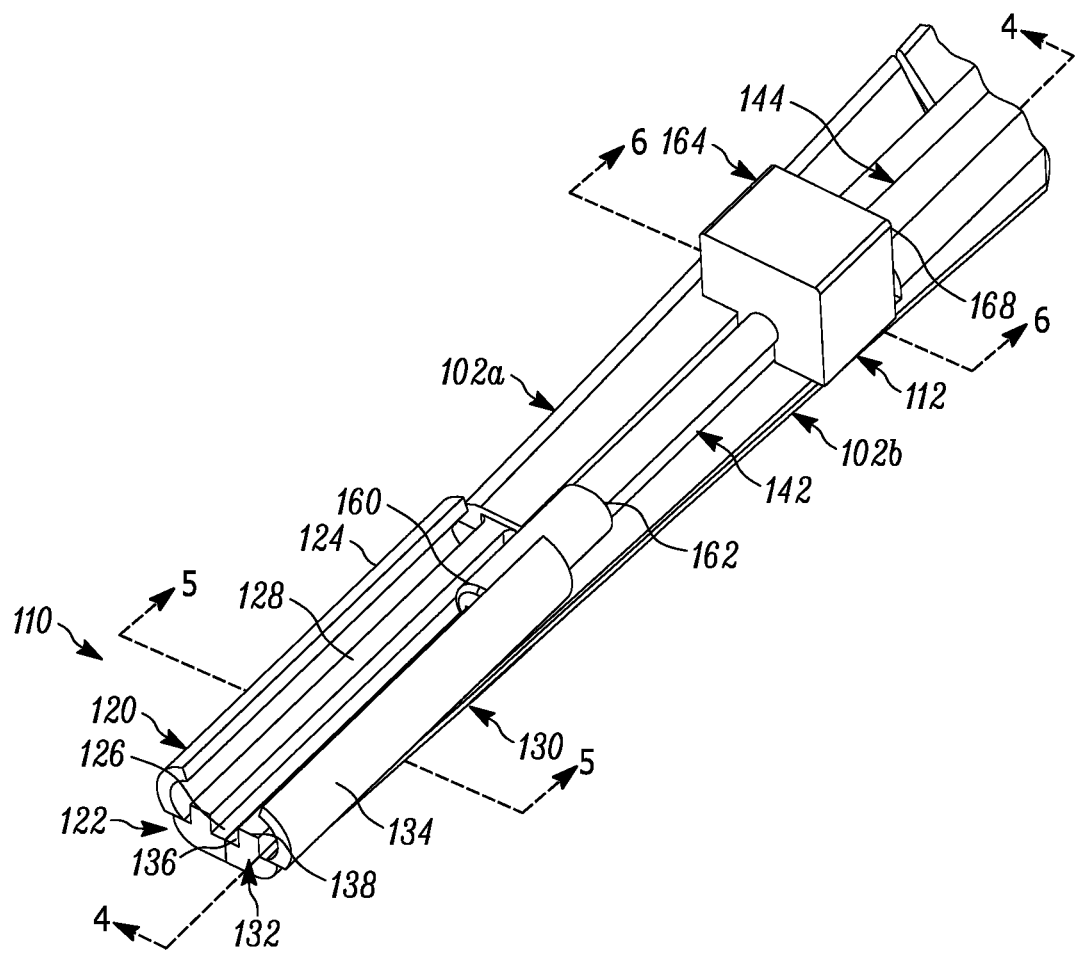
FIG. 3 of the drawings is a partial perspective view of the applicator of the present disclosure showing the opposing jaws along with the grasping element retainers and portions of the disengaging assembly.
Figure 4:
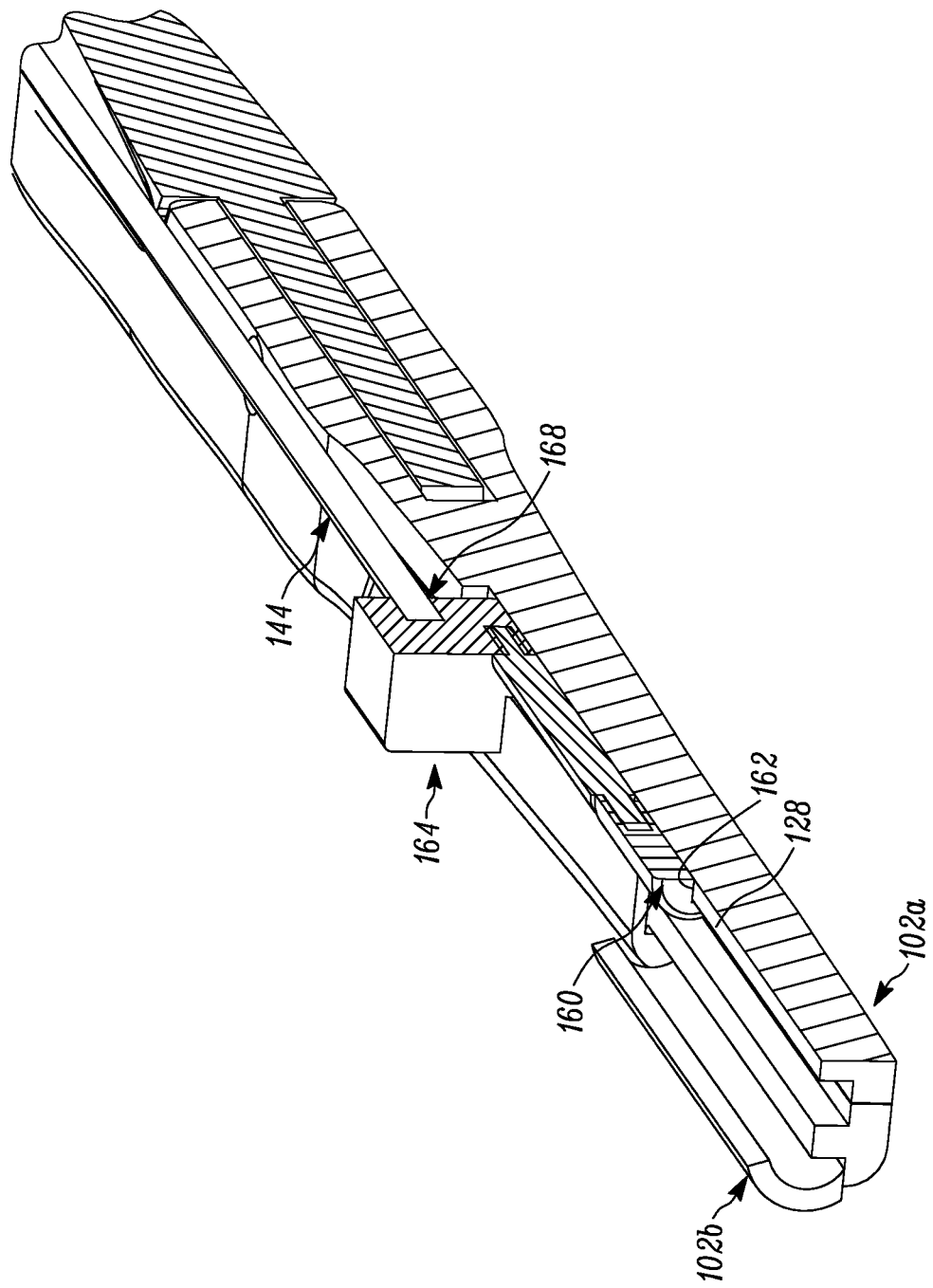
FIG. 4 of the drawings is a partial perspective cross-sectional view of the applicator of the present disclosure, taken generally about lines 4-4 of FIG. 3.
Figure 5:
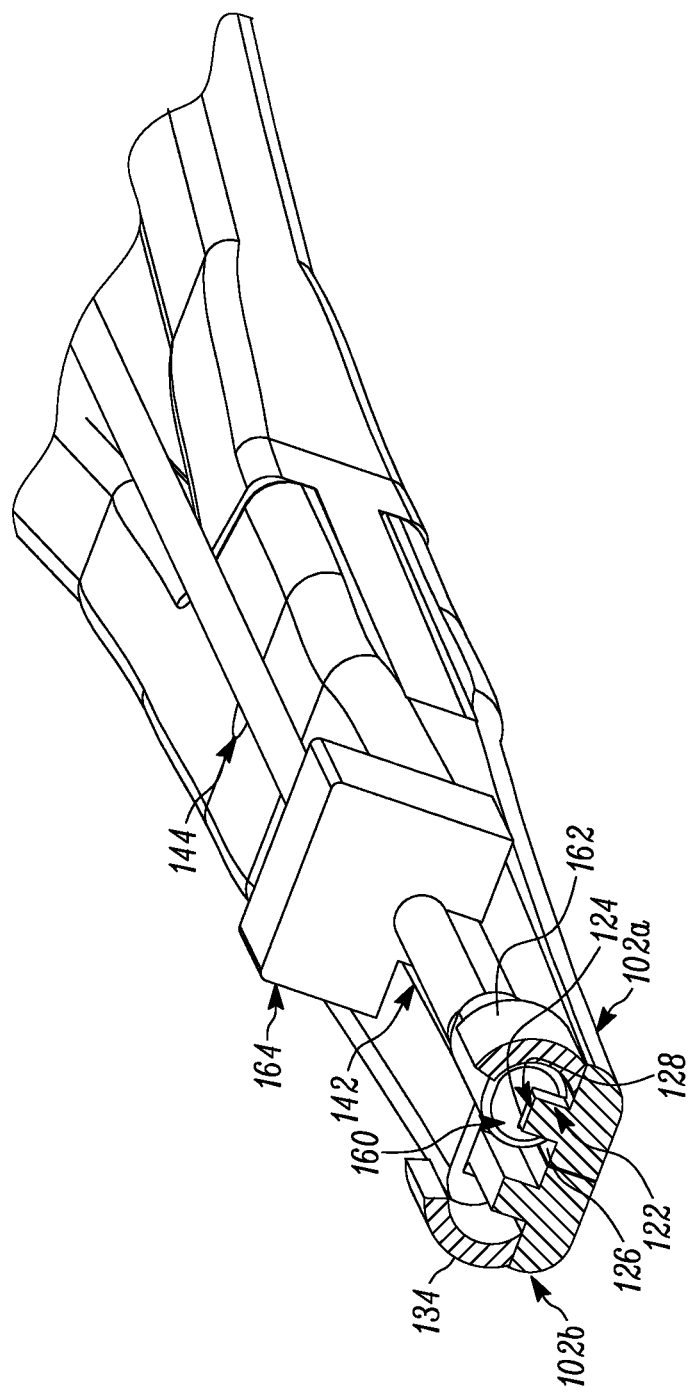
FIG. 5 of the drawings is a partial perspective cross-sectional view of the applicator of the present disclosure, taken generally about lines 5-5 of FIG. 3.
Figure 6:
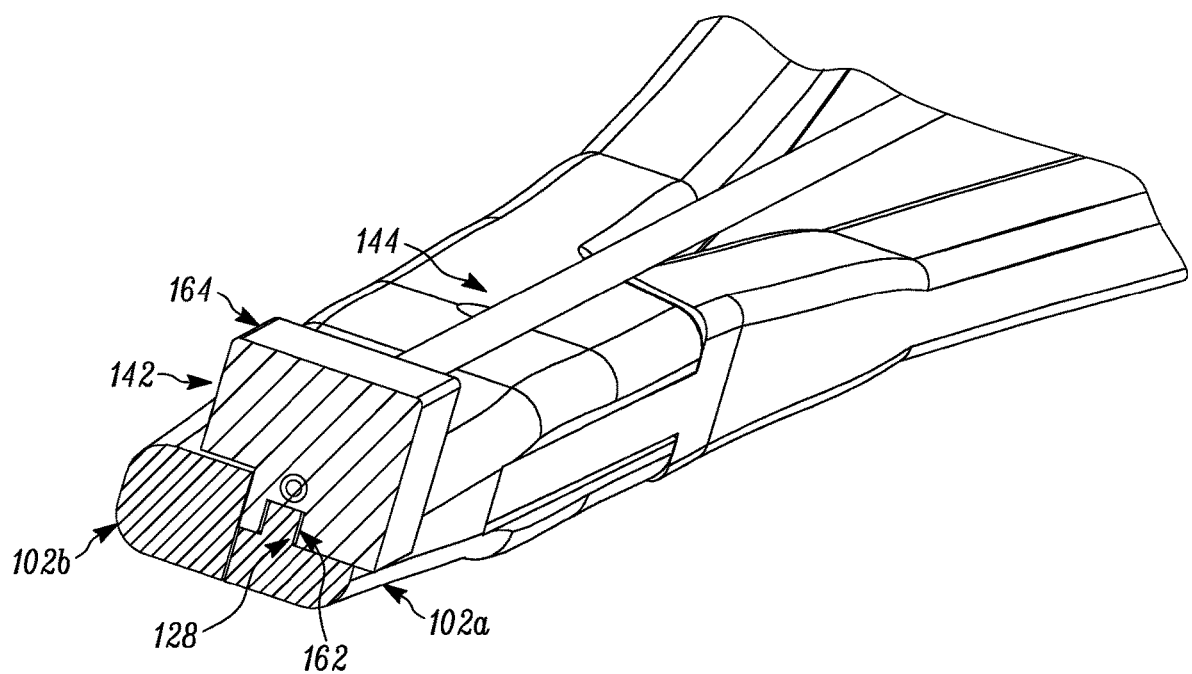
FIG. 6 of the drawings is a partial perspective cross-sectional view of the applicator of the present disclosure, taken generally about lines 6-6 of FIG. 3.

The applicator 100 further includes grasping element retainers 110 and disengaging assembly 112. With further reference to FIGS. 3, 4 and 5, the grasping element retainers 110 include first grasping element retainer 120 and second grasping element retainer 130. The first grasping element retainer is positioned on opposing jaw 102a, and includes base 122 and outer support 124. The base 122 is defined by an upper surface 126 and a mating structure 128. In the configuration shown, the mating structure 128 extends along the base 122 generally parallel to the and colinear with the opposing jaw 102a. In the configuration shown, mating structure 128 comprises an elongated tab that in cross section has a substantially square or rectangular configuration. Of course, other cross-sectional configurations are contemplated, as are slots, or other indented features or features depressed into the upper surface 126. In other configurations, the mating structure may comprise a rod or other member that extends parallel to and along the opposing jaw and that is suspended over the upper surface 126.

The outer support 124 extends along the opposing jaw 102a spaced apart from the mating structure 128. It will be understood that when the first side coupling system 20 is positioned in the proper orientation, the outer support 124 is positioned outboard of the elongated body of the coupling so as to provide outboard support, as well as movement perpendicular to the mating structure. In the configuration shown, the outer support 124 comprises an elongated arcuate member that shape matingly engages the first side tissue grasping assemblies. Such a configuration aids in the engagement of the mating structure 128 with the jaw coupling of the tissue grasping assembly. In some configurations, such outer supports 124 can be omitted.

Similarly, the second grasping element retainer 130 is a substantial mirror image of the first grasping element retainer and is positioned along the opposing jaw 102b. The second grasping element retainer 130 comprises base 132 and outer support 134. The base comprises upper surface 136 and mating structure 138. As with the mating structure 128, the mating structure 138 may have a number of configurations. Similarly, the outer support 134 extends outboard of the mating structure 138, and is configured to shape matingly engage the second side tissue grasping assembly.

In the configuration of FIGS. 20 through 25, the grasping elements may comprise the opposing jaws and the tissue grasping assemblies can be slid thereover.

As the disengaging assembly utilizes an extension of the mating structure 128, the mating structure 128 extends further along the opposing jaw 102a than the mating structure 138 extends along the opposing jaw 102b.

With further reference to FIGS. 1 through 6, the disengaging assembly 112 comprises actuator 140, plunger 142 and connecting rod 144. The actuator is at the first end of the disengaging assembly. The actuator is pivotably coupled about pivot 154 to opposing shank 106a spaced apart from the finger ring 108a, which defines a grasping handle 150 to one side of the pivot 154 and a coupling portion 152 to the other side of the pivot 154. The grasping handle 150 extends outboard of the opposing shank 106a, and may include a curved surface that facilitates engagement and manipulation by a user. The coupling portion 152 is inboard of the opposing shank 106a. As will be understood, the user can reach and pivot the actuator 140 with the index finger while other fingers are extended through or otherwise engaging the finger rings 108a, 108b to actuate and move the opposing jaws. The length of the actuator, as well as the pivot can be adjusted to achieve the desired amount of force to push against the mechanical coupling system to disengage the same.

Opposite the actuator is the plunger 142 which includes contact end 160, mating guide 162 and stop member 164. In the configuration shown, the plunger has three separate elements, whereas in other configurations, the plunger may comprise a singular element. The plunger 142 interfaces with the mating structure 128 so as to be slidably movable therealong. The contact end defines the outer surface which contacts or otherwise directs the first side coupling system 20 installed and interfaced with the mating structure 128 along the mating structure 128. The stop member 164 likewise slidably moves along the mating structure 128 of the opposing jaw 102a. The stop member may define the limits of the slidable movement of the plunger along the mating structure, on the one end contacting a stop along the opposing jaw 102a proximate the lock 104, and, on the other end contacting another structure, such as the outer support 124, defining a range of slidable movement.

In the configuration shown, when the plunger is at one end proximate the lock 104, the contact end 160 remains within the confines of the outer support 124. In other configurations, the contact end 160 may be withdrawn beyond the confines of the outer support 124.

The connecting rod 144 extends between the actuator 140 and the plunger 142 and couples the two structures together. More specifically, the first end 166 of the connecting rod 144 is pivotably coupled to the coupling portion 152 of the actuator. The second end 168 of the connecting rod 144 is, in the configuration shown, fixedly coupled to the stop member 164. It will be understood that to the extent that there is an angular displacement, the stop member may comprise a resilient but flexible member than can accommodate some angular displacement of the connecting rod while maintaining secured engagement therewith.

As will be explained below with respect to the operation, the pivoting of the actuator 140 about the pivot 154 slidably moves the plunger 142 along the opposing jaw 102a, and more specifically, along the mating structure 138. When the stop member 164 interferes with the outer support 124 of the opposing jaw 102a, further slidable movement of the plunger along the opposing jaw is substantially precluded. Pivoting in the opposite direction allows for retraction of the plunger away from the distal end 109a until, in the configuration shown, the stop member 164 interferes with a portion of the opposing jaw 102a proximate the lock 104. The amount, or range, of movement of the plunger can be determined by altering the geometry of the actuator, plunger and connecting rod and/or the relationship therebetween.

In the configuration of FIGS. 20 through 25, the disengaging assembly may be omitted, and the applicator is separated by moving the applicator after installation of the coupling system, relying on the grasping of the tissue by the coupling system to provide the necessary resistance to allow for separation.

Figure 7:
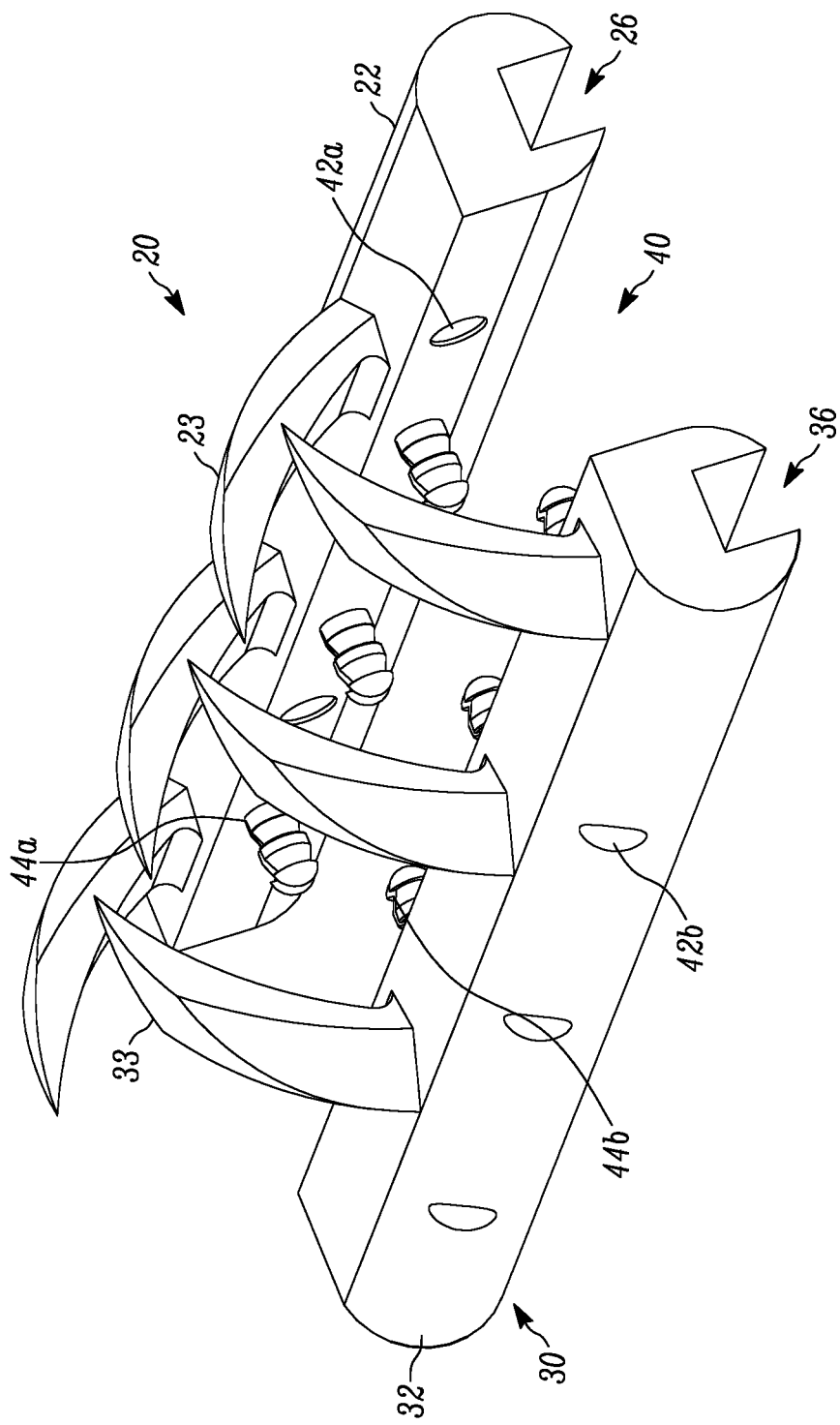
FIG. 7 of the drawings is a perspective view of the mechanical tissue coupling system of the present disclosure showing the first and second side tissue grasping assemblies, along with the joining assembly therebetween.
Figure 8:
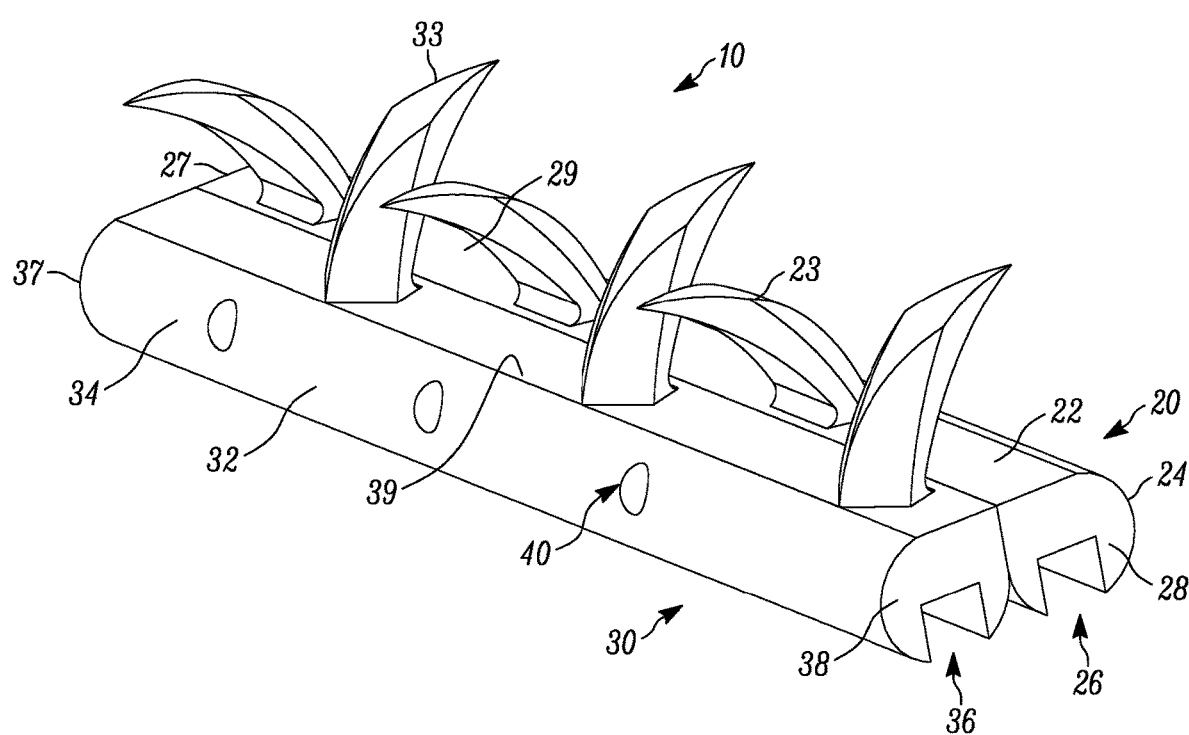
FIG. 8 of the drawings is a perspective view of the mechanical tissue coupling system of the present disclosure showing the first and second side tissue grasping assemblies in the locked configuration.
Figure 9:
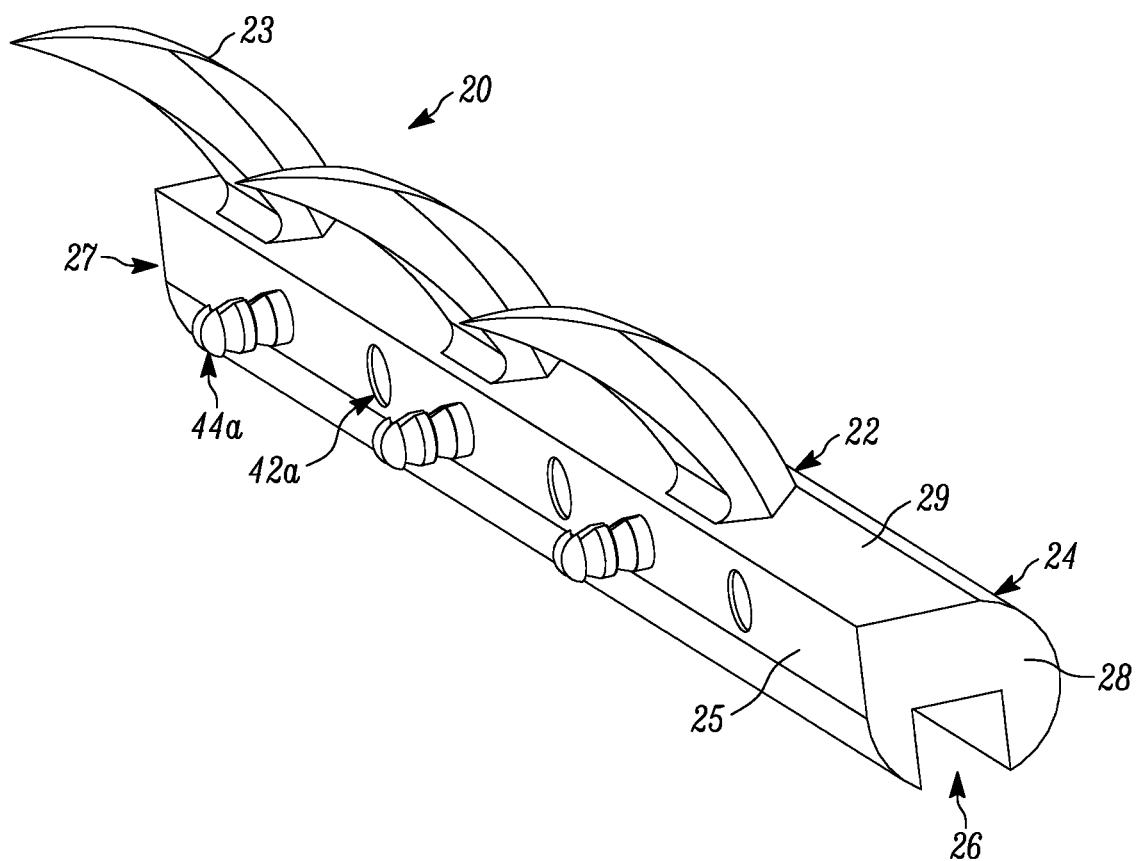
FIG. 9 of the drawings is a perspective view of the first side tissue grasping assembly with the portions of the joining assembly disposed thereon.
Figure 10:
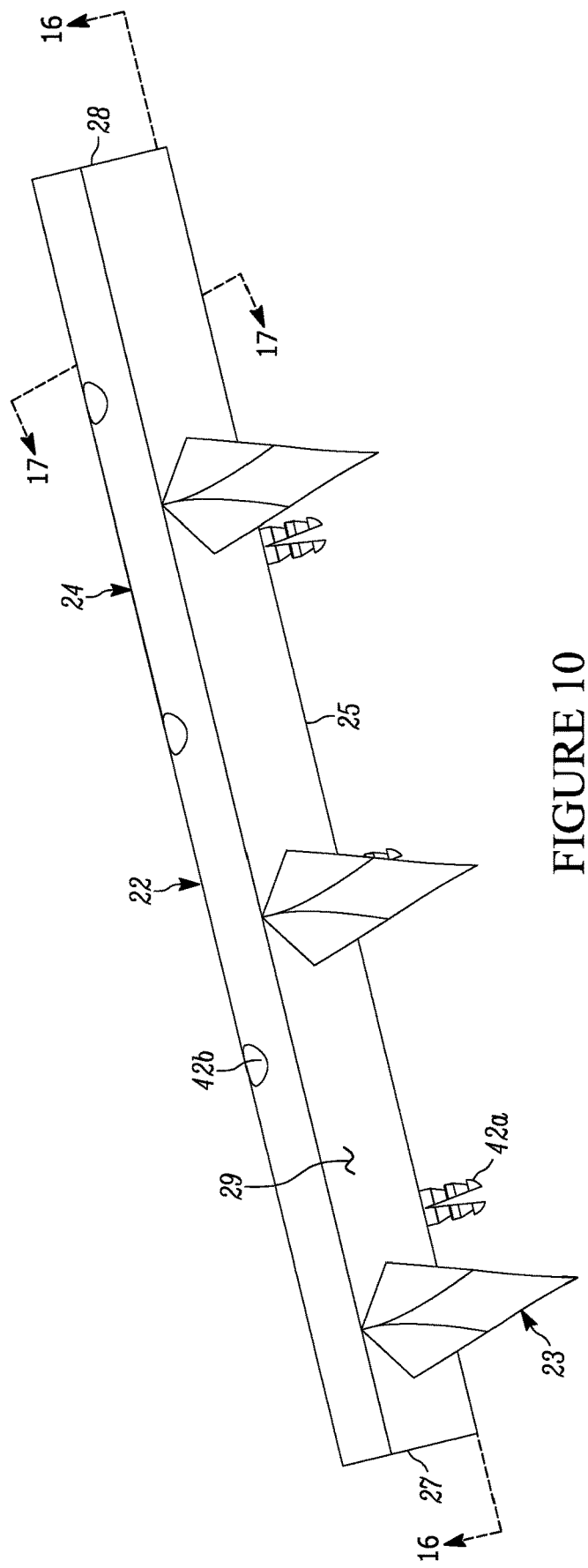
FIG. 10 of the drawings is a top plan view of the first side tissue grasping assembly with the portions of the joining assembly disposed thereon.
Figure 11:
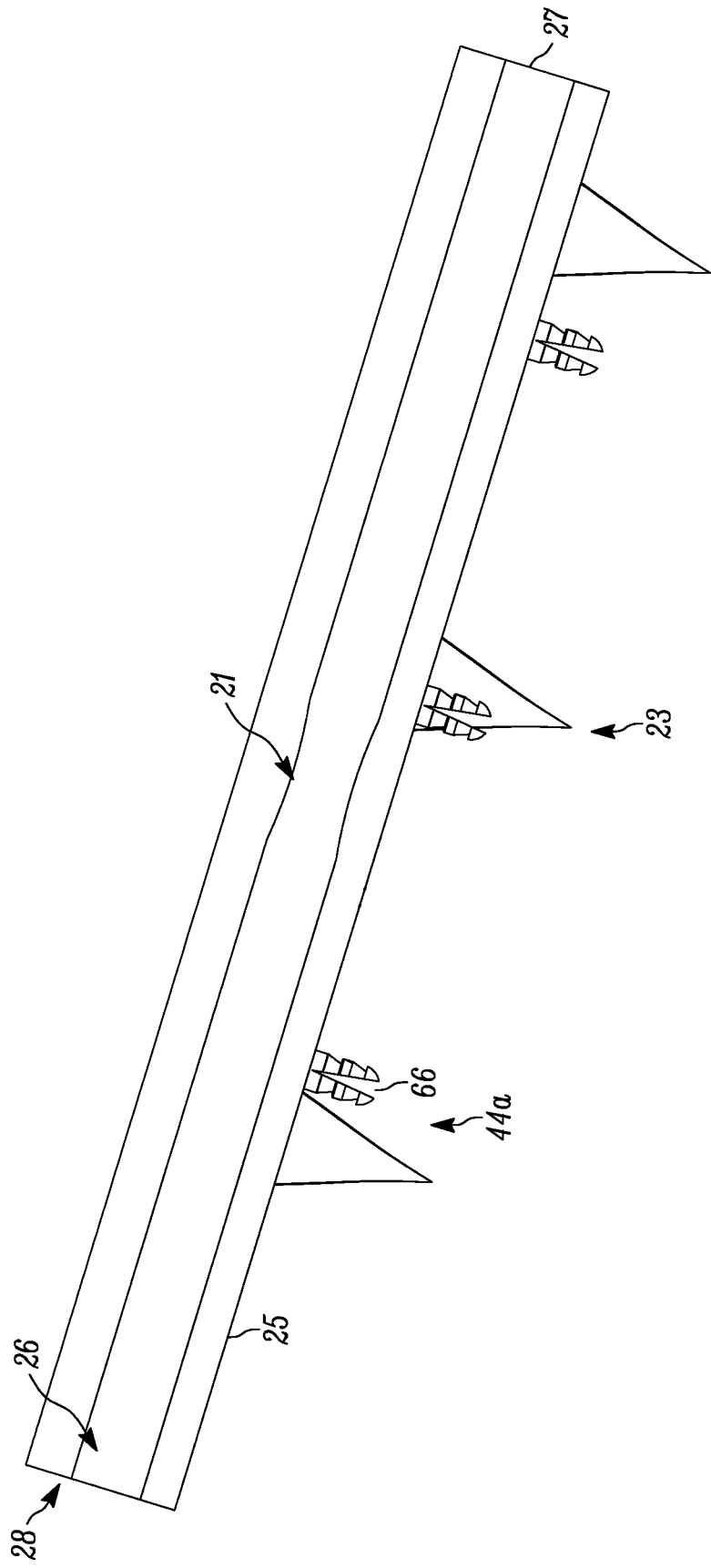
FIG. 11 of the drawings is a bottom plan view of the first side tissue grasping assembly with the portions of the joining assembly disposed thereon.
Figure 12:
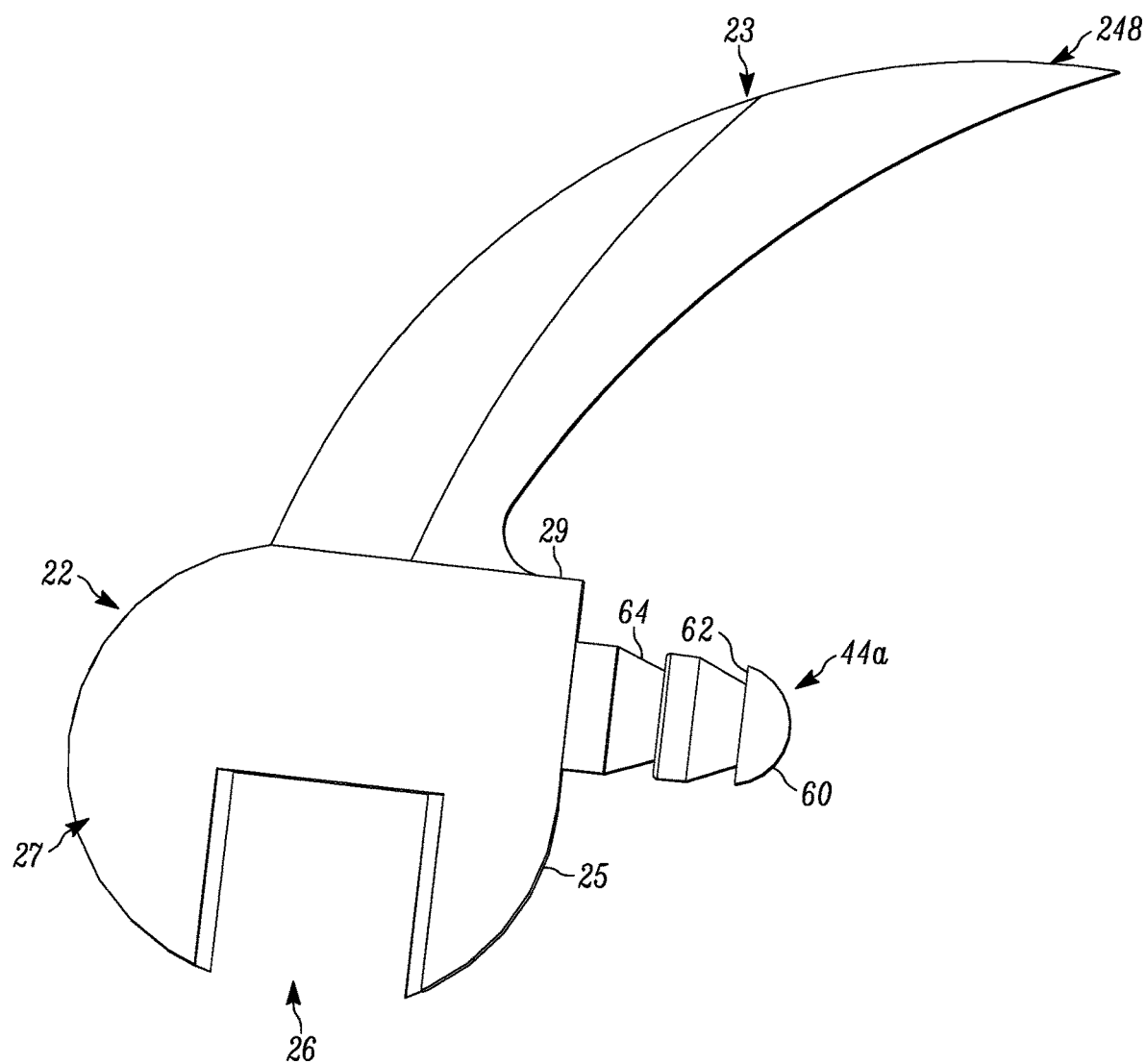
FIG. 12 of the drawings is a first side elevational view of the first side tissue grasping assembly with the portions of the joining assembly disposed thereon.
Figure 13:
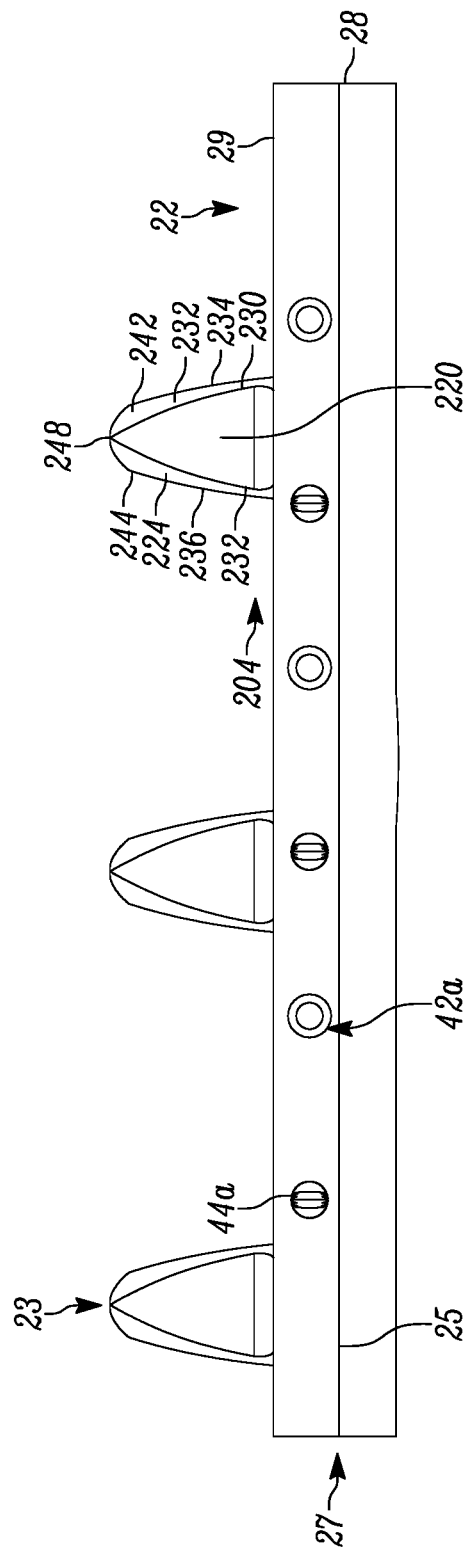
FIG. 13 of the drawings is a front elevational view of the first side tissue grasping assembly with the portions of the joining assembly disposed thereon.
Figure 14:
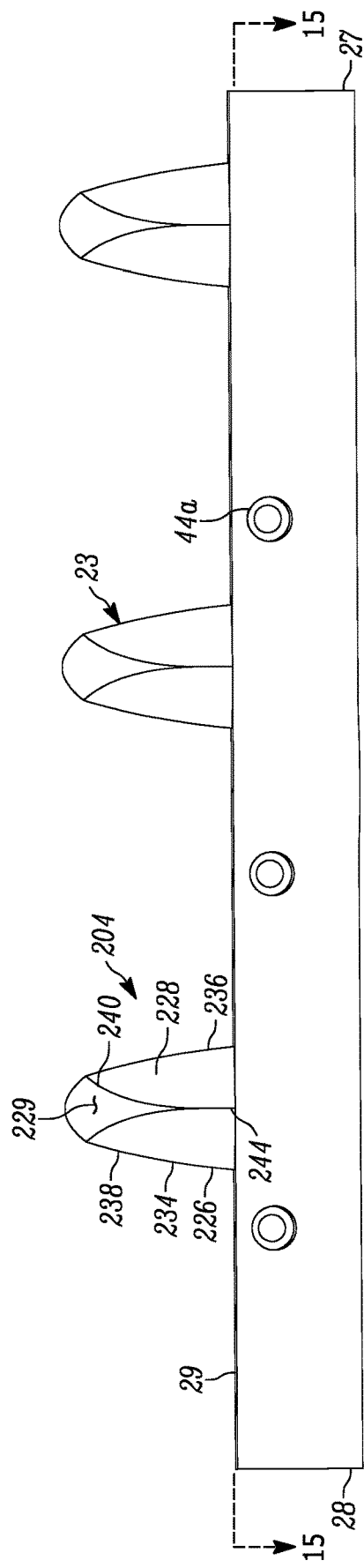
FIG. 14 of the drawings is a back elevational view of the first side tissue grasping assembly with the portions of the joining assembly disposed thereon.
Figure 15:
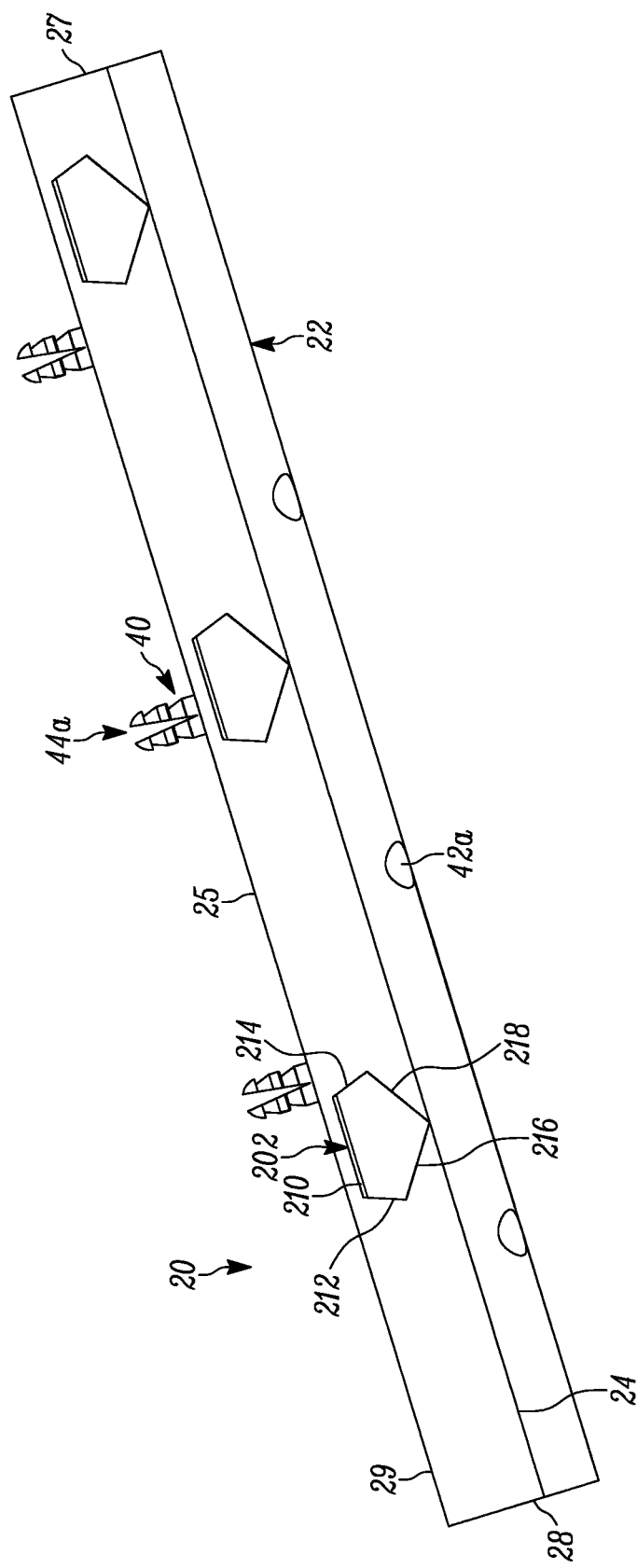
FIG. 15 of the drawings is a cross-sectional view of the first side tissue grasping assembly with the portions of the joining assembly disposed thereon, taken generally about lines 15-15 of FIG. 14.
Figure 16:
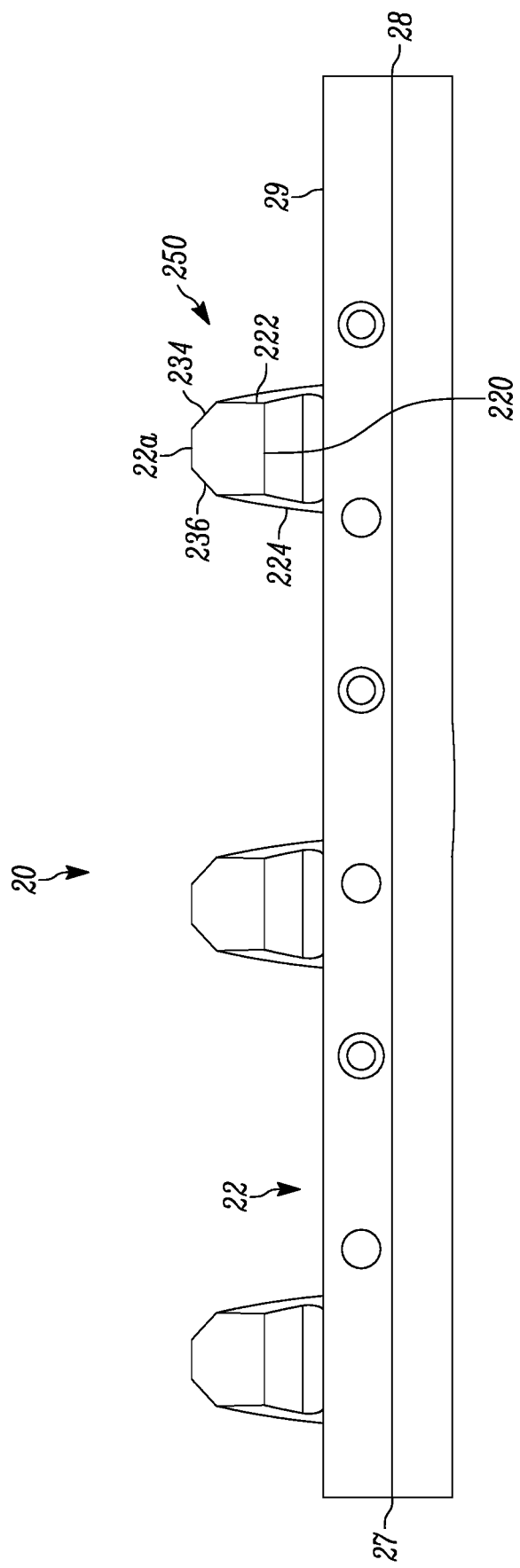
FIG. 16 of the drawing is a cross-sectional view of the first side tissue grasping assembly with the portions of the joining assembly disposed thereon, taken generally about lines 16-16 of FIG. 10.
Figure 17:
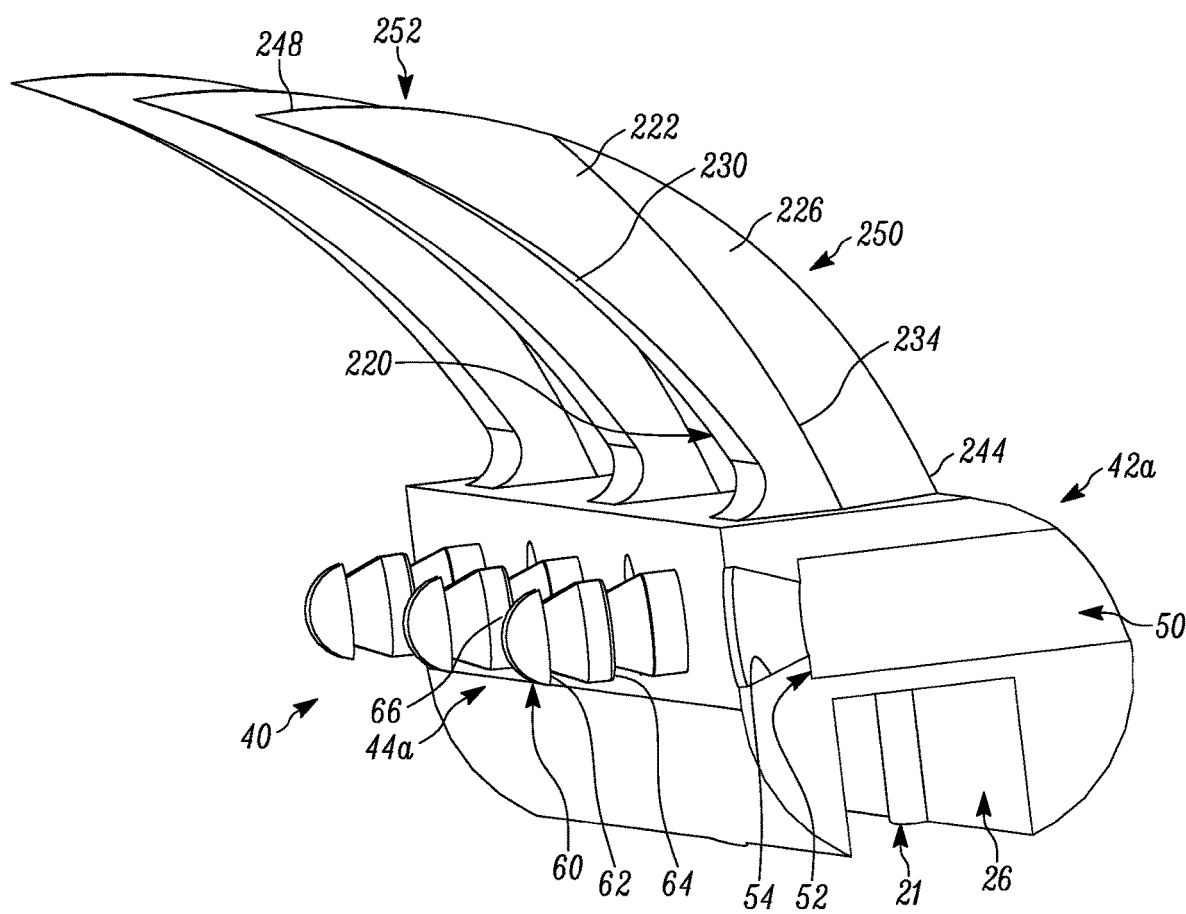
FIG. 17 of the drawings is a cross-sectional view of the first side tissue grasping assembly with the portions of the joining assembly disposed thereon, taken generally about lines 17-17 of FIG. 10.

The mechanical tissue coupling system, as shown in greater detail in FIGS. 7 and 8, comprises first side tissue grasping assembly 20, second side tissue grasping assembly 30 and joining assembly 40. A will be explained in detail below, the mechanical tissue coupling system 10 can be installed and coupled together with the aid of the applicator 100. The first and second side tissue grasping assemblies 20 and 30 comprise separate components which can be coupled together through the joining assembly 40, portions of which are found on either one of the tissue grasping assemblies. In the configuration shown, the two tissue grasping assemblies are identical with one being rotated 180° relative to the other. Advantageously, only a single part is utilized. In other configurations, it may be desirable to have the tissue grasping assemblies be distinct members.

In some configurations, the grasping assemblies comprise a polymer or composite member. In other configurations, the grasping assemblies may comprise a material which can dissolve within the body of a patient over a predetermined time. The predetermined time may comprise a few hours, a few days, a few weeks or a few months. Generally, there is no particular limitation on how long the material takes to dissolve within the body of the patient, and a number of predetermine lengths of time are contemplated. In other configurations, the gripping assemblies may be formed from entirely different material, such as, for example, a metal, such as titanium, for example.

With reference to FIGS. 9 through 17, the first side tissue grasping assembly will be described in greater detail, with the understanding that the second side tissue grasping assembly has the same structural features. The first side tissue grasping assembly comprises a body 22 and gripping structures 23. The body comprises an elongated member that has an outer surface 24 and a jaw coupling 26. The outer surface 24 includes an inner end 27, an outer end 28, a gripper region 29 and a mating region 25. In the configuration shown, the outer surface 24 generally defines a continuous member between the inner and outer end. The outboard surface of the elongated body comprises a semi-circular configuration in cross-section. In the configuration shown, the elongated body generally comprises a substantially linear member, while other configurations, such as arcuate and the like, are contemplated as well.

The jaw coupling 26 comprises a structure which can matingly engage and slide along the mating structure 128. In the configuration shown, the jaw coupling 26 comprises an elongated slot that matingly engages the mating structure 128 so as to be slidable therealong and relative thereto. In the configuration shown, a narrowed region 21 is defined along the jaw coupling, which more closely engages the mating structure 128. Such a configuration precludes inadvertent and undesirable sliding between the tissue grasping assembly and the mating structure. Additionally, the narrowed region 21 may protrude beyond the lower surface of the elongated body to also aid in the retention of the tissue grasping assembly along the mating structure. In other configurations, such as the configuration of FIGS. 20, 21 and 22, the jaw coupling may comprise a bore which is configured to receive the opposing jaw 102a so as to releasably retain the same. In still other configurations, the jaw coupling may comprise a protrusion (such as an elongated tab or the like). A number of different configurations are contemplated.

The gripping structures 23 extend outwardly from the gripper surface 29, which extends between the inner and outer ends of the outer surface. The gripping structures 23 may comprise a number of different structures which can engage tissue of a patient. In the configuration shown, the gripping structures extend over and beyond the mating surface 25 of the elongated body 22 (and over the second side coupling system when coupled thereto).

In some configurations, the gripping structures comprise those disclosed and claimed in copending U.S. patent application Ser. No. 15/801,529, filed Nov. 2, 2017, entitled "Bandage and Anchor For Bandages", the entirety of which is hereby incorporated by reference in its entirety. Some of the gripping structures which may be suitable for use are shown in U.S. Pat. App. Pub. No. 2017/0128273, filed Nov. 11, 2016, entitled "Bandage", the entirety of which is hereby incorporated by reference in its entirety. For example, in the configuration shown in FIGS. 20 through 25, a plurality of rows of gripping structures can be aligned generally perpendicular to the curvature of the elongated body. It will be understood that greater or fewer of these gripping structures, as well as fewer or greater rows or a matrix of gripping structures is contemplated.

In the configuration shown in FIGS. 7 through 17, and with particular reference to FIGS. 13-16, the gripping structures may comprise a series of gripping structures disposed on the outer surface. The gripping structures shown are generally oriented perpendicular to a longitudinal axis of the first side tissue grasping assembly. In one such configuration, the gripping structures comprise a base configuration 260 and upstanding structure 270, which is formed from a plurality of walls and edges.

The base configuration comprises a leading edge 210, first side wing edge 212, second side wing edge 214, first side trailing edge 216, and second side trailing edge 218. In the configuration shown, the leading edge is substantially parallel with the mating surface with the edges together defining a pentagon which is symmetrical about an axis perpendicular to and bisecting the leading edge. In the configuration shown, the length of the leading edge is larger than the length of the wing edges and the trailing edges, with the trailing edges being larger than the wing edges.

The upstanding structure further comprises a front curved wall 220, a first side wing wall 222, a second side wing wall 224, a first side trailing wall 226, a second side trailing wall 228 and an arcuate cap wall 229. The front curved wall extends upwardly from the leading edge 210 (and a filleted joint may be disposed thereat). The first side wing wall 222 extends upwardly from the first side wing edge. The second wing wall 224 extends upwardly from the second side wing edge. The first side trailing wall 226 extends from the first side trailing edge. The second side trailing wall 228 extends from the second side trailing edge. The first side trailing wall and the second side trailing wall meet at the back edge 246.

The arcuate cap wall 229 is defined by the first side rear cap edge 238, the second side rear cap edge 240, the first side wing leading edge 230 and the second side wing leading edge 232. The first side rear cap edge 238 extends from the back edge 246 to the first side wing trailing edge 234 and joins the arcuate cap wall 229 with the first side trailing wall. The second side rear cap edge 240 extends from the back edge 246 to the second side wing trailing edge 236. The first side front cap edge 242 extends from the first side wing trailing edge 234 to the tip 248. The second side cap edge 244 extends from the second side wing trailing edge 236 to the tip 248.

The back edge 236 meets both the first side rear cap edge 238 and the second side rear cap edge 240. The first side rear cap edge 238, the first side front cap edge 242 and the first side wing trailing edge 234 meet together. The second side rear cap edge 240, the second side front cap edge 242 and the second side wing trailing edge 236 meet together. The first side wing leading edge 230, the second side wing leading edge 234, the first side front cap edge 242, the second side front cap edge 244 meet at the tip 248.

The upstand structure 204 extends both upwardly and outwardly so as to overhang the mating surface 25 of the first side tissue grasping assembly 20, so as to define a contained portion 250 that overlies the elongated body 22 and an overhang portion 252 that extends beyond the elongated body 22. In the configuration shown, the cross-sectional configuration, taken by a plane that is coplanar with the mating surface 25, comprises a hexagon defined by the front curved wall 220, the first side wing wall 222, the second side wing wall 224, the first side trailing wall 226, the second side trailing wall 228 and the arcuate cap wall 229. By the time the tip has been reached, the first side trailing wall 226 and the second side trailing wall 228 have terminated, with the front curved wall, the first side wing wall, the second side wing wall and the arcuate cap wall remaining and meeting at the tip. The arcuate cap wall terminates at the back edge 246 spaced apart from the base configuration 202.

The arcuate cap wall defines an arcuate diamond configuration, with the front curved wall defining an arcuate three sided configuration, the first and second trailing walls forming an arcuate three sided configuration, and the first and second side wing walls forming an arcuate four sided configuration. In the configuration shown, a line tangent to the the first side front cap edge and the second side front cap edge at the tip is substantially perpendicular to the mating surface 25. It is contemplated that such a tangent at the tip, preferably, is between +/−20° and more preferably between +/−10°. Such a configuration provides enhanced retention between the gripping structures and the tissue. Of course, the disclosure is not limited to such angular relationships.

In the configuration shown, a total of three spaced apart gripping structures are presented. The three spaced apart gripping structures are spaced apart from each other a uniform distance, but, the gripping structures are offset relative to the inner end 27 and the outer end 28 so as to be closer to one of the inner end an the outer end. This is done so that when two of the same tissue grasping assemblies are coupled, the respective gripping structures are spaced apart from each other and alternate between the opposing tissue grasping assemblies.

Of course, in other configurations, other gripping structures may be employed.

As set forth above, the second side tissue grasping assembly is the same as the first side tissue grasping assembly. For purposes of describing the connection and the coupling, the second side tissue grasping assembly has been give different reference numbers. It will also be understood that, in other configurations, the two tissue grasping assemblies may be distinct. The second side tissue grasping assembly comprises body 32 and gripping structures 33. The body comprises an elongated member that has an outer surface 34 and a jaw coupling 36. The outer surface 34 includes an inner end 37, an outer end 38 and a gripper surface 39. In the configuration shown, the outer surface 34 generally defines a continuous member between the inner and outer end. The jaw coupling 36 comprises an elongated slot.

As explained above, with the gripping structures not being centered relative to the elongated body, the spaced apart gripping structures are spaced apart from each other so as to be out of phase with each other. For example, a gripping structure of the first side tissue grasping assembly extends between two adjacent gripping structures of the second side tissue grasping assembly, and vice versa.

It is contemplated that, in other configurations, the two bodies may be very different relative to each other, and may be rather distinct relative to each other. Some such differences may be due to different structural needs wherein the mechanical coupling system will be employed in the body.

The joining assembly 40 is shown as comprising a plurality of first mating structures, such as first mating structure 42 (for purposes of describing the assembly, the reference numbers for the first mating structures of the first side tissue grasping assembly 20 have been augmented with an "a" and with a "b" for the second side tissue grasping assembly), and a plurality of second mating structures, such as second mating structure 44 (similarly, the reference numbers have been augmented with an "a" for the first side tissue grasping assembly and a "b" for the second side tissue grasping assembly. The first mating structure 42 comprises a bore that is defined in the mating surface 25. In the configuration shown, the bore extends entirely through the elongated body 22. Additionally, in the configuration shown, the bore is generally perpendicular to the mating surface 25 and perpendicular to the elongated slot of the jaw coupling 26.

A narrowing portion 54 is disposed within the bore starting at or near the mating surface 25. The narrowing portion terminates at or near a retaining ledge 52. The retaining ledge represents a cross-sectional configuration that is narrower than the bore at or near the mating surface 25.

In the configuration shown, three spaced apart first mating structures. These mating structures are disposed equidistantly along the mating surface, however, they are not symmetrical about the length of the elongated body, but offset.

The second mating structure 44 comprises a tab 60 which includes outer flange 62, inner flange 64 and split channel 66. The outer flange and the inner flange are spaced apart from each other and concentric about the tab 60. A narrowed region generally precedes and succeeds the flanges. The split channel 66 extends longitudinally into the tab so that the when pinched, the cross-sectional area of the tab can be reduced.

A total of three second mating structures are disposed at predetermined intervals along the mating surface 25. The second mating structures are likewise disposed equidistantly, and generally between the first mating structures. It will be understood that when two of the tissue grasping assemblies are mated, the second mating structures of one of the tissue grasping assemblies is directed into the first mating structure of the other of the tissue grasping assemblies.

One of the mating interactions will be described with the understanding that the other mating interactions may occur generally simultaneously, and generally in the same manner. Specifically, as the tab 60 enters into the bore 50, the split channel 66 is compressed and the tab is directed along the narrowing portion 54. At some point, the outer flange 62 passes beyond the retaining ledge 54 and the tab expands so that the flange 62 is captured by the retaining ledge 54. At such time disconnecting the two requires substantially greater force. Further insertion again compresses the split channel 66 and directs the inner flange along the narrowing portion 54. At some point the inner flange 64 extends beyond the retaining ledge 52 resulting in the expansion of the tab so that the inner flange 64 is captured by the retaining ledge 54.

It will be understood that such a configuration defines two positions of locking engagement, a first when the outer flange engages the retaining ledge and a second when the inner flange engages the retaining ledge. In some instances, the that is grasped will permit only engagement of the outer flange with the retaining ledge, whereas in other instances engagement of the inner flange with the retaining ledge is achieved. It will be understood that in other configurations, additional positions of locking engagement may be provided through the incorporation of additional flanges on the tabs. In other configurations, a single position of locking engagement may be provided.

It will further be understood that different coupling mechanisms may be utilized, which permit joining of two tissue grasping assemblies in locked engagement. Furthermore, it will be understood that while multiple locking positions are facilitated by multiple structures on the second mating structure, such multiple structures may be found on the first mating structure.

Figure 18:
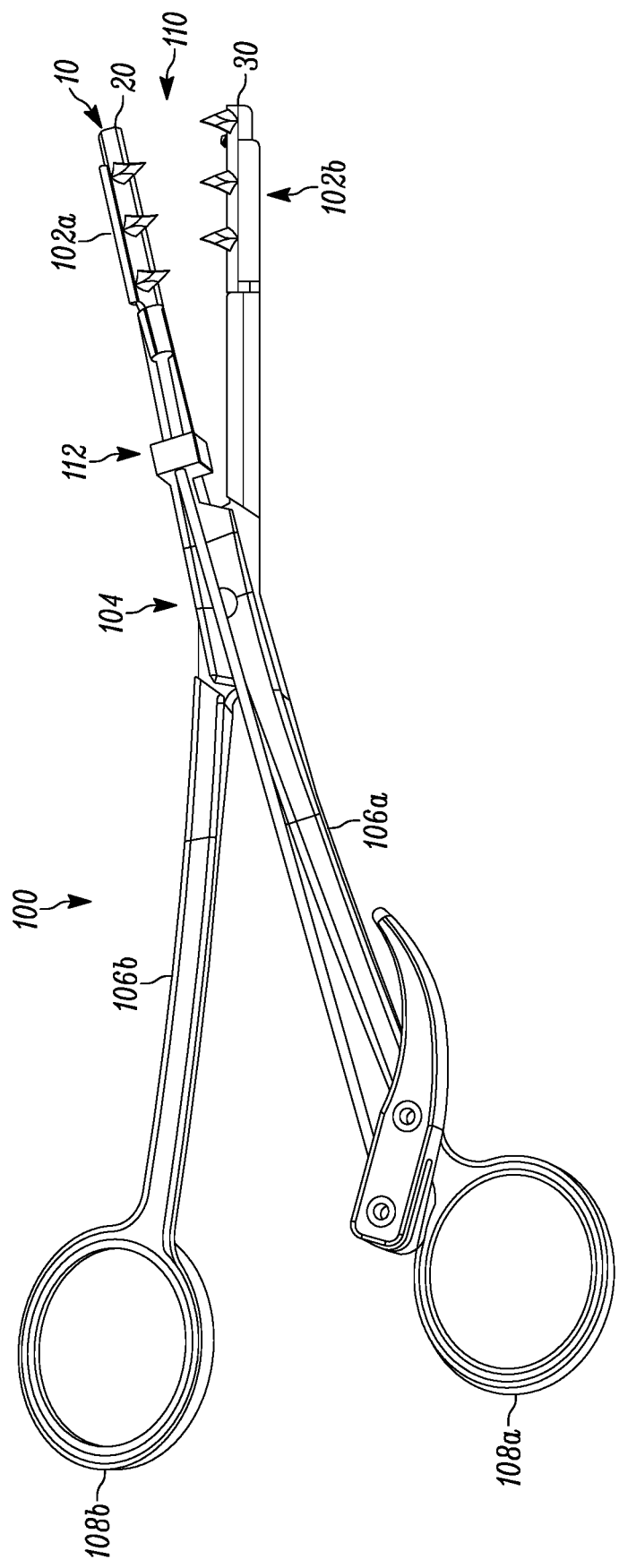
FIG. 18 of the drawings is a perspective view of the mechanical tissue coupling system and applicator of the present disclosure, showing, in particular, the system installed onto an applicator and in an unlocked configuration with the system separated by separating the opposing jaws of the forceps of the applicator.

In operation, it is contemplated that the mechanical coupling system can be utilized within a body cavity of a patient to secure tissue together. To achieve the same, the applicator 100 is first provided. Next, and with reference to FIG. 18, the opposing jaws 102a, 102b can be spread apart through relative rotation of the same about the lock 104. Once spread apart, the first side tissue grasping assembly 20 can be installed onto the opposing jaw 102a. In greater detail, the first side tissue grasping assembly 20 is directed so as to mate the jaw coupling 26 with the mating structure 128 of the first grasping element retainer 120 on the opposing jaw 102a, as the distal end 109a thereof. Once mated, the first side tissue grasping assembly 20 is slid along the mating structure until positioned in the desired position.

Similarly, the second side tissue grasping assembly can be installed onto the opposing jaw 102b. In greater detail, the second side tissue grasping assembly 30 is directed so as to mate the jaw coupling 36 with the mating structure 138 of the second grasping element retainer 130 on the opposing jaw 102b, as the distal end 109b thereof. Once mated, the second side tissue grasping assembly 30 is slid along the mating structure until positioned in the desired position, with such a configuration shown in FIG. 1. The base 132 may include a detent or other structure to limit further slidable movement of the tissue grasping assembly.

Once placed in the operable configuration, the medical practitioner can locate tissue of a patient that has been separated into a first portion and a second portion that are both separated from each other by a separation region and that is in need of joining or bringing together (and such tissue may be subcutaneous or may be on the surface of the tissue). Instead of utilizing sutures or the like, the present mechanical coupling system can be utilized. That is, the medical practitioner can grasp the forceps and separate the opposing jaws from each other through rotation thereof about the lock 104. Next, the medical practitioner can direct the respective gripping structures into tissue. It will be understood that the gripping structures of the first side tissue grasping assembly is positioned on one side of the tissue to be joined, with the gripping structures of the second side tissue grasping assembly is positioned on the other side of the tissue to be joined. Once the gripping structures have been directed into the respective tissue, the user can bring the opposing jaws toward each other by rotating the shanks toward each other about the lock.

As the first side and the second side tissue grasping assemblies reach each other and touch each other, the first mating structure of the joining assembly found on the first side tissue grasping assembly and the second mating structure of the joining assembly found on the second side tissue grasping assembly engage each other. Continued forcing of the two structures directs the tabs of the second mating structures into the respective one of the bores of the first mating structures. Eventually, as explained above, the outer flanges engage the retaining ledges of the respective bores coupling the first side tissue grasping assembly to the second side tissue grasping assembly in a locked engagement. In some instances, the user may further direct the first and second side tissue grasping assemblies toward each other which can direct the inner flange of the second mating structures beyond the retaining ledge of the first mating structures. Such a mated configuration (with tissue positioned therebetween not shown) is shown in FIG. 1.

Figure 19:
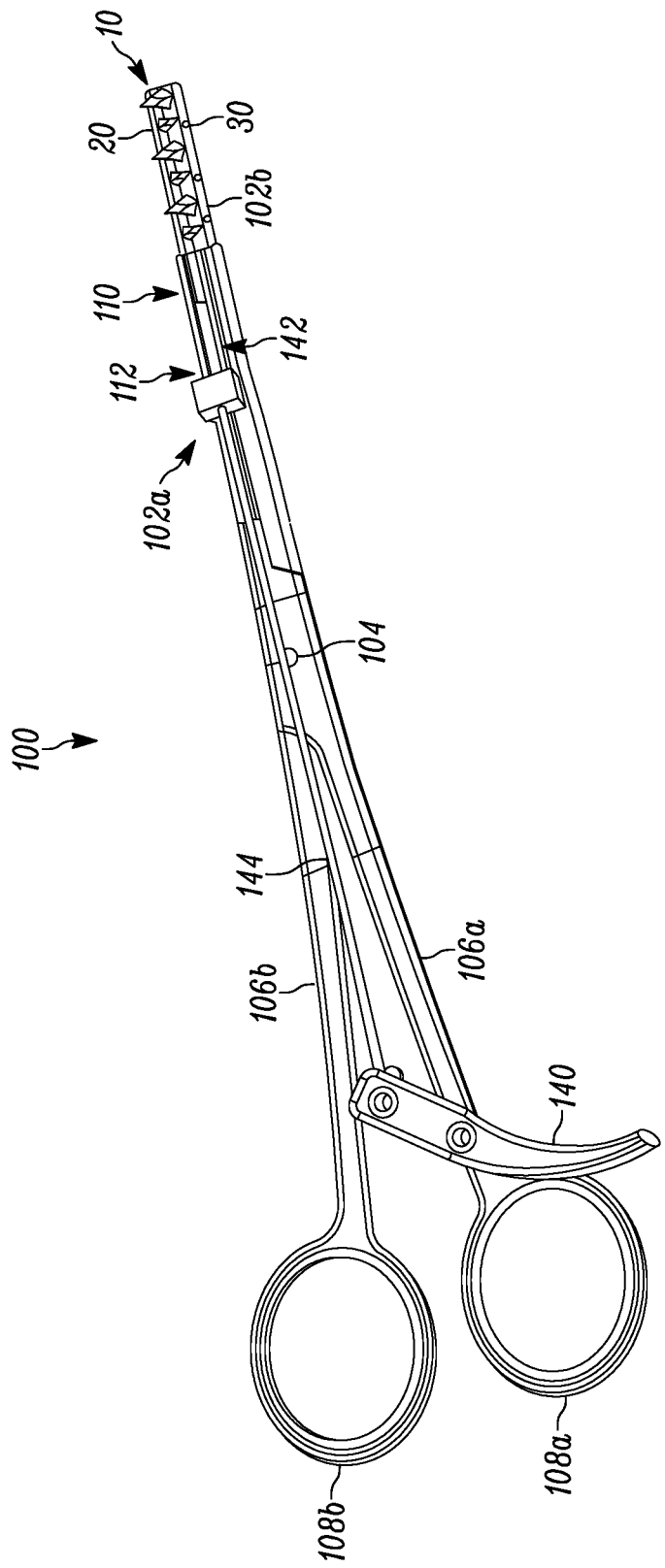
FIG. 19 of the drawings is a perspective view of the mechanical tissue coupling system and applicator of the present disclosure, showing, in particular, the system installed onto an applicator and in a locked configuration (the second position of locking therebetween), and being disengaged from the applicator by actuation of the disengaging assembly through pivoting of the actuator.
Figure 20:
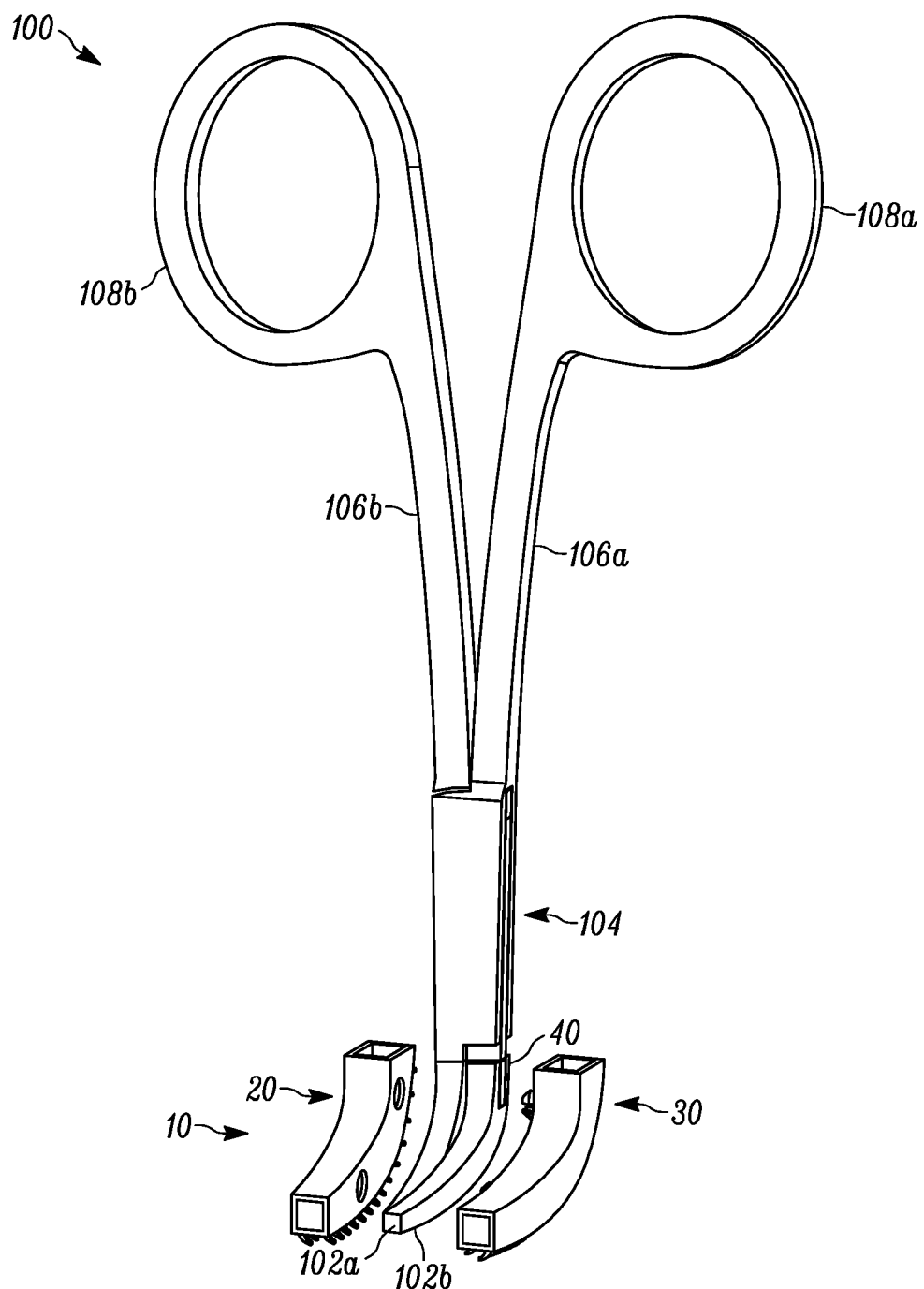
FIG. 20 of the drawings is perspective view of another configuration the mechanical coupling system of the present disclosure, positioned proximate to the applicator which can be utilized therewith.
Figure 21:
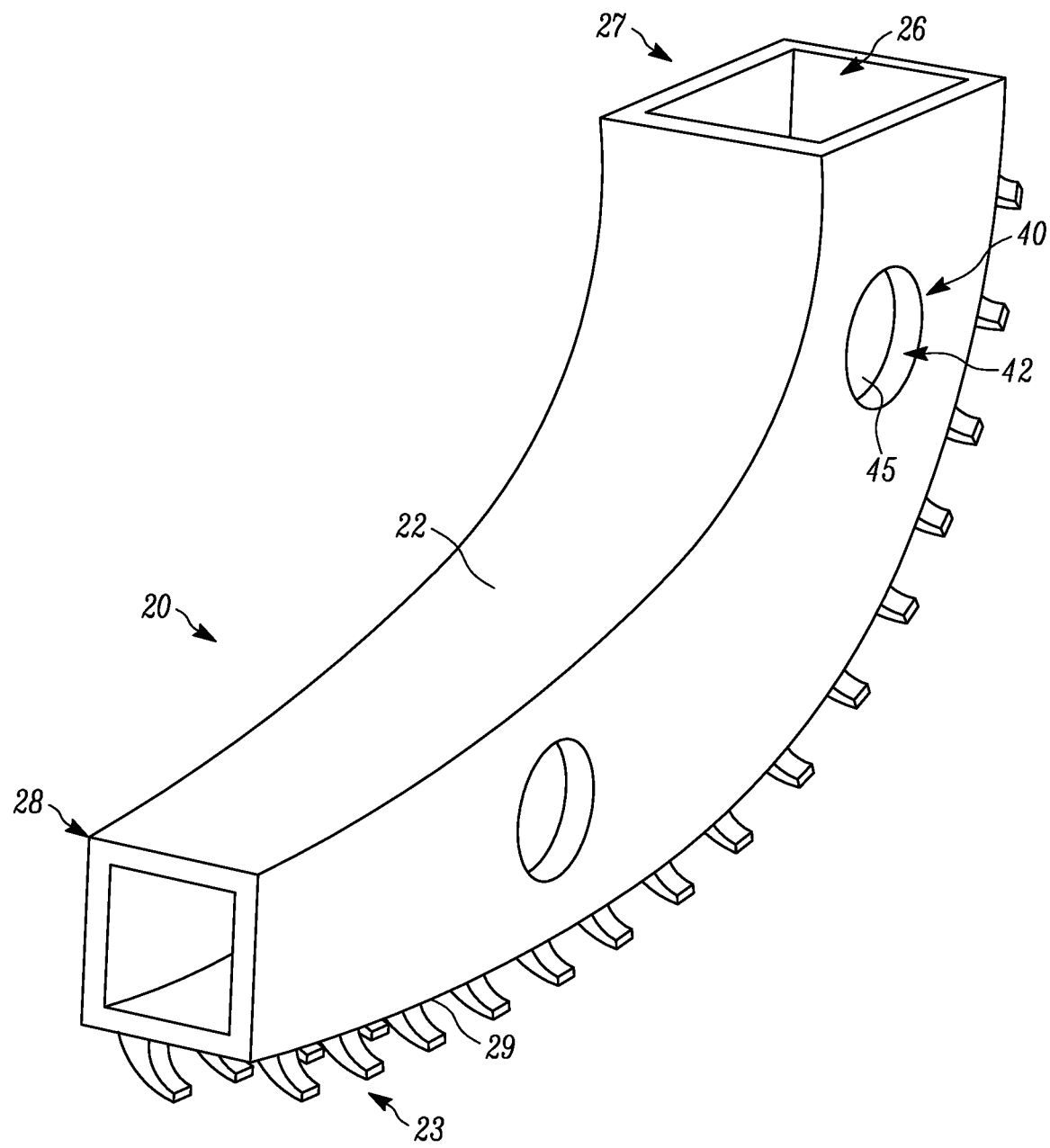
FIG. 21 of the drawings is a front perspective view of the first side tissue grasping assembly of the mechanical coupling system of the present disclosure shown in FIG. 20.
Figure 22:
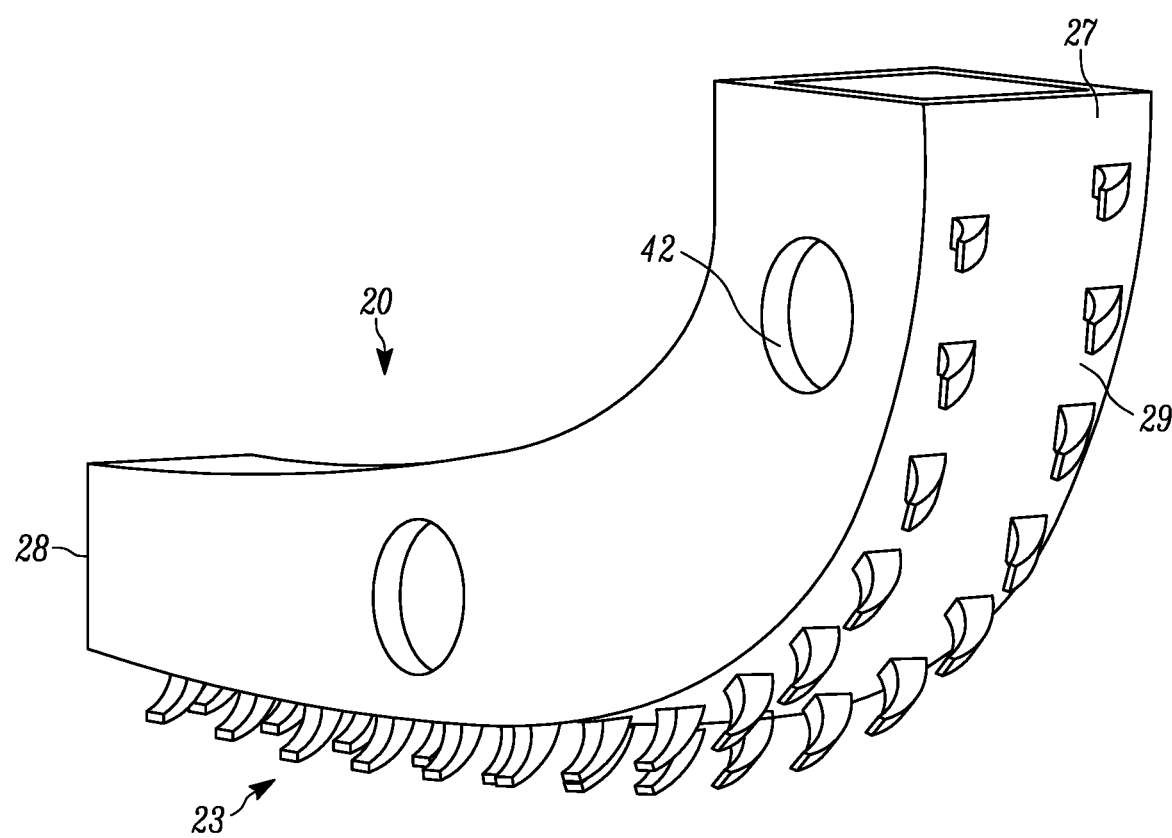
FIG. 22 of the drawings is a back perspective view of the first side tissue grasping assembly of the mechanical coupling system of the present disclosure shown in FIG. 20.
Figure 23:
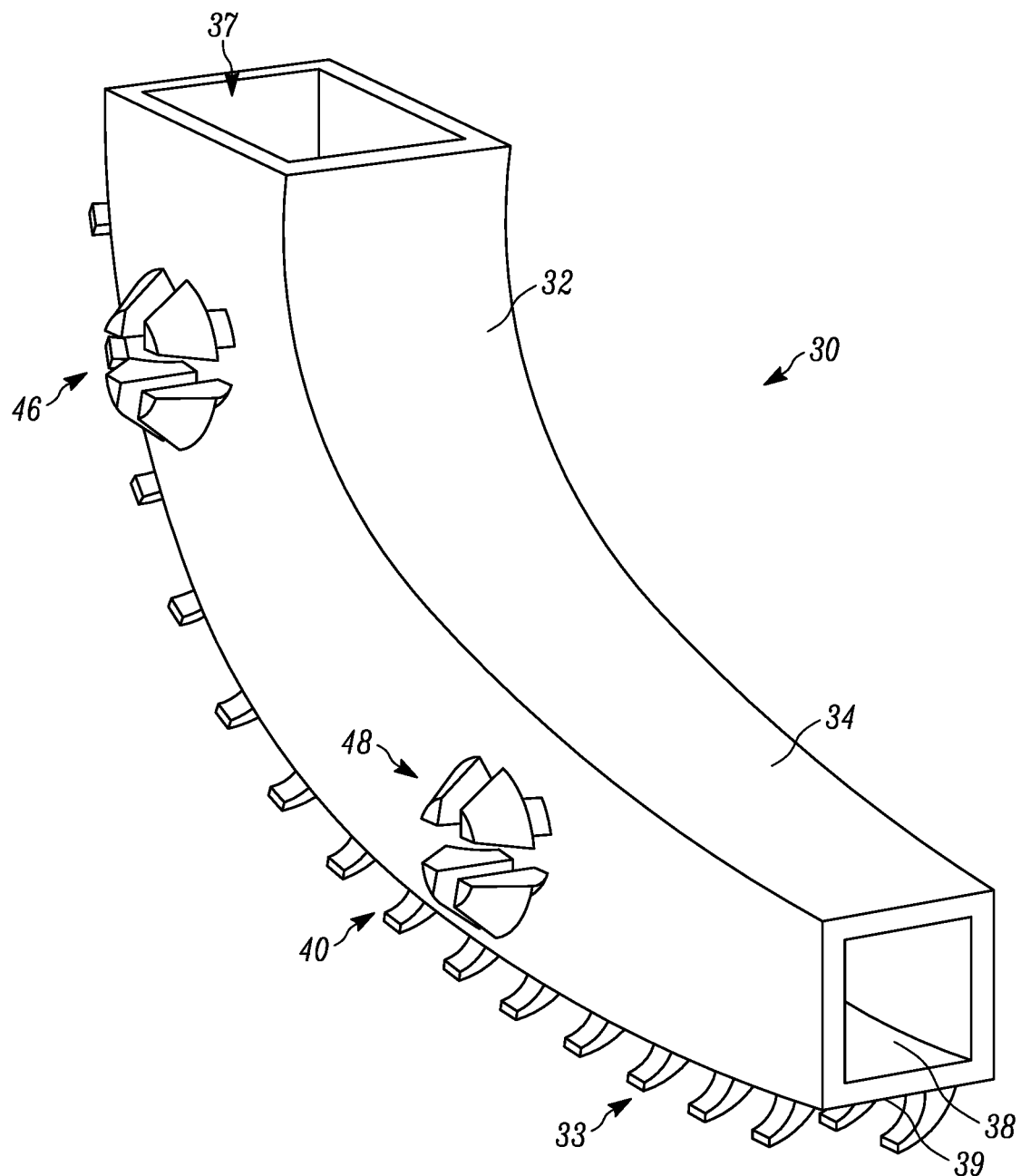
FIG. 23 of the drawings is a front perspective view of the second side tissue grasping assembly of the mechanical coupling system of the present disclosure shown in FIG. 20.
Figure 24:
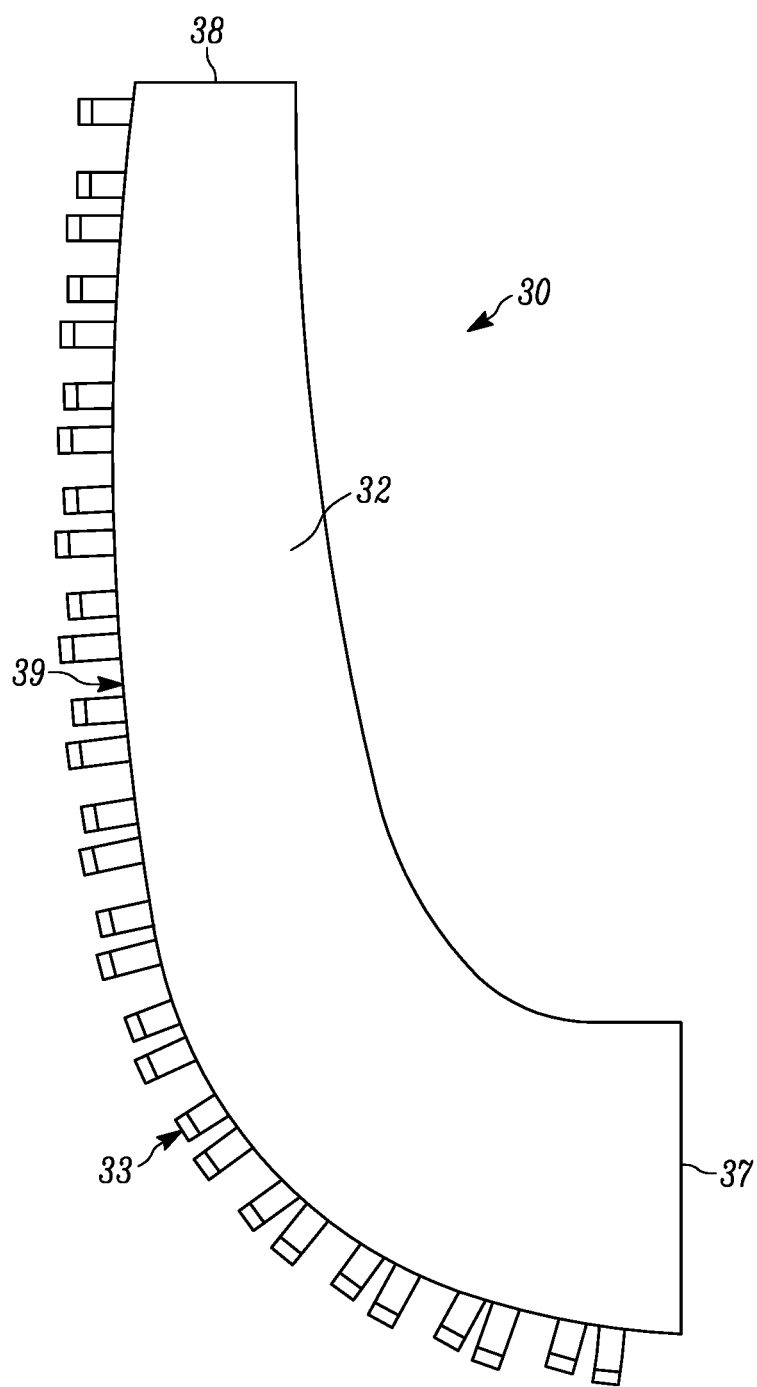
FIG. 24 of the drawings is an outside elevational view of the second side tissue grasping assembly of the mechanical coupling system of the present disclosure shown in FIG. 20.
Figure 25:
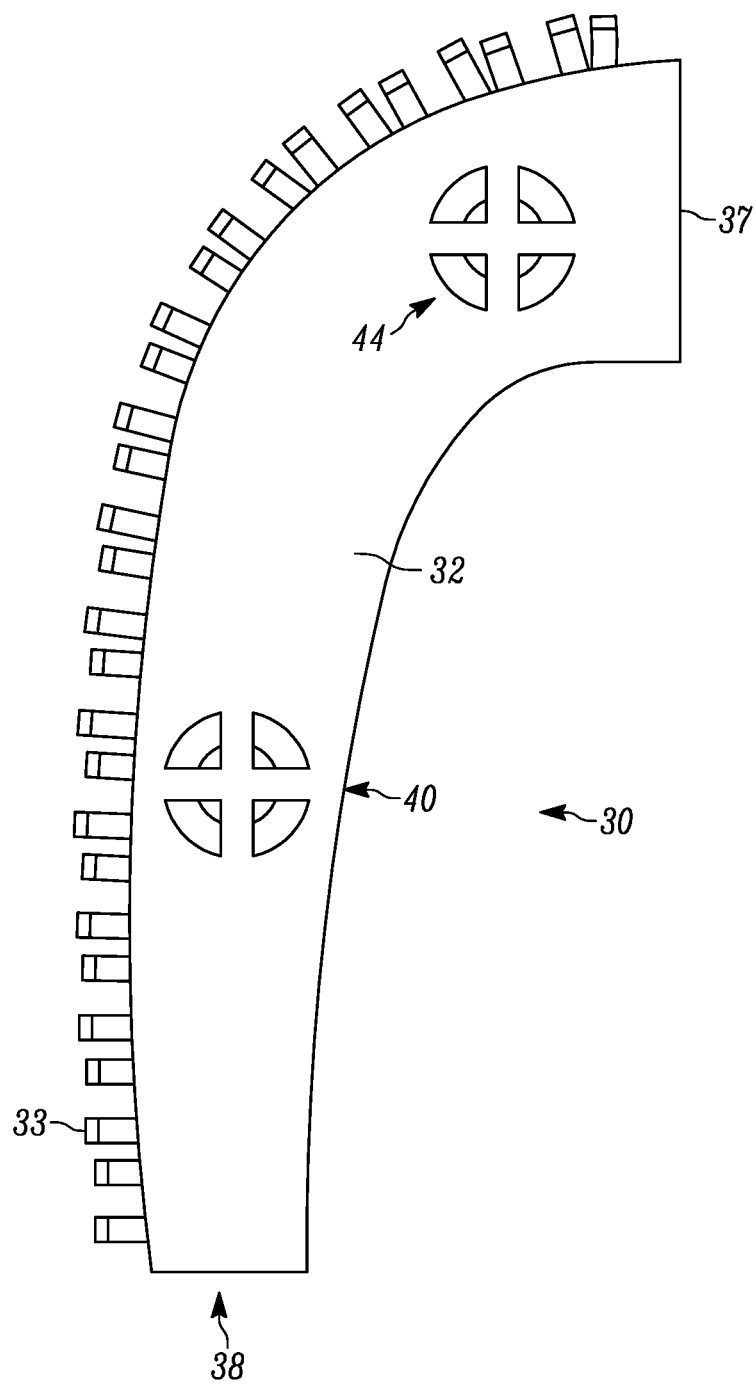
FIG. 25 of the drawings is an inside elevational view of the second side tissue grasping assembly of the mechanical coupling system of the present disclosure shown in FIG. 20.

Once the first side tissue grasping assembly and the second side tissue grasping assembly are matingly joined through the joining assembly, the user can decouple the mechanical coupling system from the applicator through the disengaging assembly. More specifically, and with reference to FIG. 19, the user can pivot the actuator 140 relative to the shank 106a so as to direct the coupling portion toward the opposing jaws. Such a pivoting, directs the connecting rod 144 toward the distal end 109a, 109b of the opposing jaws. As the connecting rod 144 is coupled to the plunger, the plunger is slidably moved along the mating structure 128 pushing the joined first and second side tissue grasping assemblies outwardly away from the applicator. Continued pivoting of the actuator eventually directs the entirety of the first and second tissue grasping assemblies beyond the distal ends 109a, 109b of the opposing jaws and decouples the mechanical coupling system from the applicator. The applicator can then be moved away from the mechanical coupling system, and, the wound.

In the configuration of FIGS. 20-25, the user merely disengages the applicator by pulling the applicator away from the mechanical tissue coupling system while the system is engaging tissue.

In certain configurations, the first and second side tissue grasping assemblies can remain permanently with in the body cavity of the user, coupled to the tissue. In other configurations, the tissue grasping assemblies can be removed in a second, or subsequent procedure. In still other configurations, the tissue grasping assemblies may be utilized solely during a procedure, and can be removed prior to completion of the procedure.

In still other configurations, the tissue grasping assemblies can be formed of materials that can dissolve within the body cavity after a predetermined amount of time, as explained above. In such instances, the tissue grasping assemblies can, over time, dissolve and/or disappear within the body.

It will be understood that various different configurations are contemplated of varying size and shape, depending on the manner in which and the location wherein the tissue grasping assemblies will be utilized. It will further be understood that the size of the gripping structures can be varied, as well as the shape thereof, depending on the type of tissue with which the gripping structures will be utilized, as well as the location of use, and the type of use. It will further be understood that the first and second side tissue grasping assemblies may be manually installed on a patient, that is without forceps and/or other tools or the like.

The foregoing description merely explains and illustrates the disclosure and the disclosure is not limited thereto except insofar as the appended claims are so limited, as those skilled in the art who have the disclosure before them will be able to make modifications without departing from the scope of the disclosure.

What is claimed is:

1. An applicator structurally configured to apply a mechanical tissue coupling system, the applicator comprising:
    forceps defining a first opposing jaw and a second opposing jaw, the first opposing jaw attached to a first opposing shank and the second opposing jaw attached to a second opposing shank and pivotably coupled by a lock;
    a first grasping element retainer disposed on the first opposing jaw, the first grasping element retainer structurally configured to allow slidable engagement of a first tissue grasping assembly therealong, the first tissue grasping assembly comprising a first mating surface, a first elongated body having an inner end and an outer end, a first jaw coupling disposed on the first elongated body, and a first plurality of tissue gripping structures extending over and beyond the first mating surface;
    a second grasping element retainer disposed on the second opposing jaw, the second grasping element retainer structurally configured to allow slidable engagement of a second tissue grasping assembly therealong, the second tissue grasping assembly comprising a second mating surface, a second elongated body having an inner end and an outer end, a second jaw coupling disposed on the second elongated body, and a second plurality of tissue gripping structures extending over and beyond the second mating surface, the first mating surface to mate against the second mating surface; and
    a disengaging assembly having an actuator pivotably coupled to the first opposing shank, with a plunger slidably movable along the first opposing jaw, and a connecting rod extending between the actuator and the plunger, such that, pivoting of the actuator slidably moves the plunger along the first opposing jaw toward or away from a distal end of the first opposing jaw.

2. The applicator of claim 1 wherein the first grasping element retainer further includes a mating structure extending along the first opposing jaw and the second grasping element retainer further includes a mating structure extending along the second opposing jaw.

3. The applicator of claim 2 wherein the first grasping element retainer further includes an outer support extending along the first opposing jaw and positioned outboard of the mating structure extending along the first opposing jaw; and the second grasping element retainer further includes an outer support extending along the second opposing jaw and positioned outboard of the mating structure extending along the second opposing jaw.

4. The applicator of claim 2 wherein the plunger slidably moves along the mating structure extending along the first opposing jaw.

5. A combination mechanical tissue coupling system and applicator, wherein the mechanical tissue coupling system comprises:
    a first side tissue grasping assembly comprising a first mating surface, a first elongated body having an inner end and an outer end, a first jaw coupling disposed on the first elongated body, and a first plurality of tissue gripping structures extending over and beyond the first mating surface;
    a second side tissue grasping assembly comprising a second mating surface, a second elongated body having an inner end and an outer end, a second jaw coupling disposed on the second elongated body, and a second plurality of tissue gripping structures extending over and beyond the second mating surface, the first mating surface to mate against the second mating surface; and
    a joining assembly structurally configured to join the first side tissue grasping assembly to the second side tissue grasping assembly, and,
    the applicator comprises:
    forceps defining a first opposing jaw and a second opposing jaw, the first opposing jaw attached to a first opposing shank and the second opposing jaw attached to a second opposing shank and pivotably coupled by a lock;
    a first grasping element retainer disposed on the first opposing jaw, the first grasping element retainer structurally configured to allow slidable engagement of the first side tissue grasping assembly therealong;

a second grasping element retainer disposed on the second opposing jaw, the second grasping element retainer structurally configured to allow slidable engagement of the second side tissue grasping assembly therealong; and a disengaging assembly having an actuator pivotably coupled to the first opposing shank, with a plunger slidably movable along the first opposing jaw, and a connecting rod extending between the actuator and the plunger, such that, pivoting of the actuator slidably moves the plunger along the first opposing jaw toward or away from a distal end of the first opposing jaw.

6. The combination mechanical tissue coupling system and applicator of claim 5 wherein each of the first and second jaw couplings comprise an elongated slot extending between the inner end and the outer end of the first and second elongated bodies.

7. The combination mechanical tissue coupling system and applicator of claim 6 wherein each of the first and second plurality of tissue gripping structures include an upstand structure that extends both upward and outward and that terminates in a tip.

8. The combination mechanical tissue coupling system and applicator of claim 7 wherein the tip is part of the an overhang portion.

9. The combination mechanical tissue coupling system and applicator of claim 5 wherein the first and second plurality of tissue gripping structures are equally spaced relative to each other while being offset and not centered relative to the first and second elongated bodies.

10. The combination mechanical tissue coupling system and applicator of claim 5 wherein the first side tissue grasping assembly and the second side tissue grasping assembly are substantially identical, and are one of dissolvable and non-disolvable within a body of a patient.

11. The combination mechanical tissue coupling system and applicator of claim 5 wherein the joining assembly further comprises at least one first mating structure disposed on the first side tissue grasping assembly and at least one second mating structure disposed on the second side tissue grasping assembly.

12. The combination mechanical tissue coupling system and applicator of claim 11 wherein the at least one first mating structure comprises a bore extending into the first elongated body, with the at least one second mating structure comprising a tab extendable into the bore and engageable with the bore in a locked engagement.

13. The combination mechanical tissue coupling system and applicator of claim 11 wherein the at least one first mating structure and the at least one second mating structure define at least two locking positions, varying the space between the first side tissue grasping assembly and the second side tissue grasping assembly.

14. The combination mechanical tissue coupling system and applicator of claim 13 wherein the at least one first mating structure includes a retaining ledge and the at least one second mating structure comprises an outer flange and an inner flange spaced apart from the outer flange, the outer flange engageable with the retaining ledge to define a first locked position and the inner flange engageable with the retaining ledge to define a second locked position.

15. The combination mechanical tissue coupling system and applicator claim 5 wherein the first side tissue grasping assembly includes at least one first mating structure and at least one second mating structure, and wherein the second side tissue grasping assembly includes at least one first mating structure and at least one second mating structure, the at least one first mating structure of the first side tissue grasping assembly engageable with the at least one second mating structure of the second side tissue grasping assembly and the at least one second mating structure of the first side tissue grasping assembly engageable with the at least one first mating structure of the second side grasping assembly.

* * * * *